(12) United States Patent
Litscher et al.

(10) Patent No.: US 11,801,090 B2
(45) Date of Patent: Oct. 31, 2023

(54) EXPANDABLE CATHETER AND RELATED METHODS OF MANUFACTURE AND USE

(71) Applicant: Boston Scientific Scimed, Inc., Maple Grove, MN (US)

(72) Inventors: Eric Karl Litscher, Hopkinton, MA (US); Joseph A. Levendusky, Groton, MA (US); Man Minh Nguyen, Harvard, MA (US); Paul Mannion, Shrewsbury, MA (US); TJ Byrne, County Monaghan (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 963 days.

(21) Appl. No.: 16/598,221

(22) Filed: Oct. 10, 2019

(65) Prior Publication Data
US 2020/0054391 A1 Feb. 20, 2020

Related U.S. Application Data

(63) Continuation of application No. 14/454,383, filed on Aug. 7, 2014, now Pat. No. 10,478,247.
(Continued)

(51) Int. Cl.
*A61B 18/14* (2006.01)
*A61B 17/12* (2006.01)
*A61B 18/00* (2006.01)

(52) U.S. Cl.
CPC .... *A61B 18/1492* (2013.01); *A61B 17/12104* (2013.01); *A61B 2018/0016* (2013.01);
(Continued)

(58) Field of Classification Search
CPC ........... A61B 2018/00267; A61B 2018/00273; A61B 2018/00214; A61B 2018/00279
See application file for complete search history.

(56) References Cited

U.S. PATENT DOCUMENTS 612,724 A   10/1898  Jonathan
1,155,169 A  9/1915  Starkweather
(Continued)

FOREIGN PATENT DOCUMENTS

CN    1617689 A    5/2005
CN  101309651 A   11/2008
(Continued)

OTHER PUBLICATIONS

An S.S., et al., "Airway Smooth Muscle Dynamics: A Common Pathway of Airway Obstruction in Asthma," European Respiratory Journal, 2007, 29 (5), 834-860.
(Continued)

*Primary Examiner* — Ronald Hupczey, Jr.
(74) *Attorney, Agent, or Firm* — Bookoff McAndrews, PLLC

(57) ABSTRACT

A medical device may include an expandable energy delivery array reciprocally movable between a first configuration and a second configuration. The expandable energy delivery array may include a first assembly having a first proximal end piece, a first distal end piece, and one or more first energy transfer elements extending between the first proximal and first distal end pieces, and a second assembly having a second proximal end piece, a second distal end piece, and one or more second energy transfer elements extending between the second proximal and second distal end pieces. The second proximal end piece may be proximal to the first proximal end piece and the second distal end piece may be distal to the first distal end piece.

20 Claims, 16 Drawing Sheets

Related U.S. Application Data

(60) Provisional application No. 61/864,292, filed on Aug. 9, 2013.

(52) U.S. Cl.
CPC ............... *A61B 2018/00083* (2013.01); *A61B 2018/00136* (2013.01); *A61B 2018/00214* (2013.01); *A61B 2018/00267* (2013.01); *A61B 2018/00541* (2013.01); *A61B 2018/00577* (2013.01); *A61B 2018/00821* (2013.01); *A61B 2018/1467* (2013.01)

(56) References Cited

U.S. PATENT DOCUMENTS

| | | | |
|---|---|---|---|
| 1,207,479 A | 12/1916 | Bisgaard | |
| 1,216,183 A | 2/1917 | Charles | |
| 2,072,346 A | 3/1937 | Smith | |
| 3,320,957 A | 5/1967 | Edward | |
| 3,568,659 A | 3/1971 | Karnegis | |
| 3,667,476 A | 6/1972 | Muller | |
| 3,692,029 A | 9/1972 | Adair | |
| 3,995,617 A | 12/1976 | Watkins et al. | |
| 4,095,602 A | 6/1978 | Leveen | |
| 4,116,589 A | 9/1978 | Rishton | |
| 4,129,129 A | 12/1978 | Amrine | |
| 4,154,246 A | 5/1979 | Leveen | |
| 4,461,283 A | 7/1984 | Doi | |
| 4,502,490 A | 3/1985 | Evans et al. | |
| 4,503,855 A | 3/1985 | Maslanka | |
| 4,512,762 A | 4/1985 | Spears | |
| 4,522,212 A | 6/1985 | Gelinas et al. | |
| 4,557,272 A | 12/1985 | Carr | |
| 4,565,200 A | 1/1986 | Cosman | |
| 4,567,882 A | 2/1986 | Heller | |
| 4,584,998 A | 4/1986 | McGrail | |
| 4,612,934 A | 9/1986 | Borkan | |
| 4,621,642 A | 11/1986 | Chen | |
| 4,621,882 A | 11/1986 | Krumme | |
| 4,625,712 A | 12/1986 | Wampler | |
| 4,643,186 A | 2/1987 | Rosen et al. | |
| 4,646,737 A | 3/1987 | Hussein et al. | |
| 4,674,497 A | 6/1987 | Ogasawara | |
| 4,683,890 A | 8/1987 | Hewson | |
| 4,704,121 A | 11/1987 | Moise | |
| 4,706,688 A | 11/1987 | Don Michael et al. | |
| 4,709,698 A | 12/1987 | Johnston et al. | |
| 4,739,759 A | 4/1988 | Rexroth et al. | |
| 4,754,065 A | 6/1988 | Levenson et al. | |
| 4,754,752 A | 7/1988 | Ginsburg et al. | |
| 4,765,959 A | 8/1988 | Fukasawa | |
| 4,772,112 A | 9/1988 | Zider et al. | |
| 4,773,899 A | 9/1988 | Spears | |
| 4,779,614 A | 10/1988 | Moise | |
| 4,784,135 A | 11/1988 | Blum et al. | |
| 4,790,305 A | 12/1988 | Zoltan et al. | |
| 4,799,479 A | 1/1989 | Spears | |
| 4,802,492 A | 2/1989 | Grunstein | |
| 4,817,586 A | 4/1989 | Wampler | |
| 4,825,871 A | 5/1989 | Cansell | |
| 4,827,935 A | 5/1989 | Geddes et al. | |
| 4,846,152 A | 7/1989 | Wampler et al. | |
| 4,862,886 A | 9/1989 | Clarke et al. | |
| 4,895,557 A | 1/1990 | Moise et al. | |
| 4,906,229 A | 3/1990 | Wampler | |
| 4,907,589 A | 3/1990 | Cosman | |
| 4,908,012 A | 3/1990 | Moise et al. | |
| 4,944,722 A | 7/1990 | Carriker et al. | |
| 4,955,377 A | 9/1990 | Lennox et al. | |
| 4,967,765 A | 11/1990 | Turner et al. | |
| 4,969,865 A | 11/1990 | Hwang et al. | |
| 4,976,709 A | 12/1990 | Sand | |
| 4,985,014 A | 1/1991 | Orejola | |
| 4,991,603 A | 2/1991 | Cohen et al. | |
| 5,009,636 A | 4/1991 | Wortley et al. | |
| 5,009,936 A | 4/1991 | Yamanaka et al. | |
| 5,010,892 A | 4/1991 | Colvin et al. | |
| 5,019,075 A | 5/1991 | Spears et al. | |
| 5,027,829 A | 7/1991 | Larsen | |
| 5,030,645 A | 7/1991 | Kollonitsch | |
| 5,036,848 A | 8/1991 | Hewson | |
| 5,053,033 A | 10/1991 | Clarke | |
| 5,056,519 A | 10/1991 | Vince | |
| 5,074,860 A | 12/1991 | Gregory et al. | |
| 5,078,716 A | 1/1992 | Doll | |
| 5,084,044 A | 1/1992 | Quint | |
| 5,096,916 A | 3/1992 | Skupin | |
| 5,100,388 A | 3/1992 | Behl et al. | |
| 5,100,423 A | 3/1992 | Fearnot | |
| 5,103,804 A | 4/1992 | Abele et al. | |
| 5,105,826 A | 4/1992 | Smits et al. | |
| 5,106,360 A | 4/1992 | Ishiwara et al. | |
| 5,107,830 A | 4/1992 | Younes | |
| 5,114,423 A | 5/1992 | Kasprzyk et al. | |
| 5,116,864 A | 5/1992 | March et al. | |
| 5,117,828 A | 6/1992 | Metzger et al. | |
| 5,135,517 A | 8/1992 | Mccoy | |
| 5,152,286 A | 10/1992 | Sitko et al. | |
| 5,156,151 A * | 10/1992 | Imran ................... A61N 1/056 600/375 |
| 5,165,420 A | 11/1992 | Strickland | |
| 5,167,223 A | 12/1992 | Koros et al. | |
| 5,170,803 A | 12/1992 | Hewson et al. | |
| 5,174,288 A | 12/1992 | Bardy et al. | |
| 5,188,602 A | 2/1993 | Nichols | |
| 5,191,883 A | 3/1993 | Lennox et al. | |
| 5,213,576 A | 5/1993 | Abiuso et al. | |
| 5,215,103 A | 6/1993 | Desai | |
| 5,231,996 A | 8/1993 | Bardy et al. | |
| 5,232,444 A | 8/1993 | Just et al. | |
| 5,234,456 A | 8/1993 | Silvestrini | |
| 5,254,088 A | 10/1993 | Lundquist et al. | |
| 5,255,678 A | 10/1993 | Deslauriers et al. | |
| 5,255,679 A | 10/1993 | Imran | |
| 5,265,604 A | 11/1993 | Vince | |
| 5,269,758 A | 12/1993 | Taheri | |
| 5,281,218 A | 1/1994 | Imran | |
| 5,292,331 A | 3/1994 | Boneau | |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A | 6/1994 | Imran | |
| 5,343,936 A | 9/1994 | Beatenbough et al. | |
| 5,345,936 A | 9/1994 | Pomeranz et al. | |
| 5,366,443 A | 11/1994 | Eggers et al. | |
| 5,368,591 A | 11/1994 | Lennox et al. | |
| 5,370,644 A | 12/1994 | Langberg | |
| 5,370,679 A | 12/1994 | Atlee, III | |
| 5,374,287 A | 12/1994 | Rubin | |
| 5,383,917 A | 1/1995 | Desai et al. | |
| 5,393,207 A | 2/1995 | Maher et al. | |
| 5,394,880 A | 3/1995 | Atlee, III | |
| 5,396,887 A | 3/1995 | Imran | |
| 5,400,778 A | 3/1995 | Jonson et al. | |
| 5,400,783 A | 3/1995 | Pomeranz et al. | |
| 5,411,025 A | 5/1995 | Webster | |
| 5,415,166 A | 5/1995 | Imran | |
| 5,415,656 A | 5/1995 | Tihon et al. | |
| 5,417,687 A | 5/1995 | Nardella et al. | |
| 5,422,362 A | 6/1995 | Vincent et al. | |
| 5,423,744 A | 6/1995 | Gencheff et al. | |
| 5,423,811 A | 6/1995 | Imran et al. | |
| 5,425,023 A | 6/1995 | Haraguchi et al. | |
| 5,425,703 A | 6/1995 | Feiring | |
| 5,425,811 A | 6/1995 | Mashita | |
| 5,431,696 A | 7/1995 | Atlee, III | |
| 5,433,730 A | 7/1995 | Alt | |
| 5,437,665 A | 8/1995 | Munro | |
| 5,443,470 A | 8/1995 | Stern et al. | |
| 5,454,782 A | 10/1995 | Perkins | |
| 5,456,667 A | 10/1995 | Ham et al. | |
| 5,458,596 A | 10/1995 | Lax et al. | |
| 5,465,717 A | 11/1995 | Imran et al. | |
| 5,471,982 A | 12/1995 | Edwards et al. | |

(56) References Cited

U.S. PATENT DOCUMENTS

| | | |
|---|---|---|
| 5,474,530 A | 12/1995 | Passafaro et al. |
| 5,478,309 A | 12/1995 | Sweezer et al. |
| 5,496,271 A | 3/1996 | Burton et al. |
| 5,496,311 A | 3/1996 | Abele et al. |
| 5,496,312 A | 3/1996 | Klicek |
| 5,500,011 A | 3/1996 | Desai |
| 5,505,728 A | 4/1996 | Ellman et al. |
| 5,505,730 A | 4/1996 | Edwards |
| 5,507,791 A | 4/1996 | Sit'ko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,558,073 A | 9/1996 | Pomeranz et al. |
| 5,562,608 A | 10/1996 | Sekins et al. |
| 5,571,074 A | 11/1996 | Buckman et al. |
| 5,571,088 A | 11/1996 | Lennox et al. |
| 5,574,059 A | 11/1996 | Regunathan et al. |
| 5,578,072 A | 11/1996 | Barone et al. |
| 5,582,609 A | 12/1996 | Swanson et al. |
| 5,588,432 A | 12/1996 | Crowley |
| 5,588,812 A | 12/1996 | Taylor et al. |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,623,940 A | 4/1997 | Daikuzono |
| 5,624,439 A | 4/1997 | Edwards et al. |
| 5,626,618 A | 5/1997 | Ward et al. |
| 5,630,425 A | 5/1997 | Panescu et al. |
| 5,630,794 A | 5/1997 | Lax et al. |
| 5,634,471 A | 6/1997 | Fairfax et al. |
| 5,641,326 A | 6/1997 | Adams |
| 5,647,870 A * | 7/1997 | Kordis .................. A61B 5/287 606/41 |
| 5,678,535 A | 10/1997 | DiMarco |
| 5,680,860 A | 10/1997 | Imran |
| 5,681,280 A | 10/1997 | Rusk et al. |
| 5,681,308 A | 10/1997 | Edwards et al. |
| 5,687,723 A | 11/1997 | Avitall |
| 5,688,267 A | 11/1997 | Panescu et al. |
| 5,693,078 A | 12/1997 | Desai et al. |
| 5,694,934 A | 12/1997 | Edelman |
| 5,695,471 A | 12/1997 | Wampler |
| 5,699,799 A | 12/1997 | Xu et al. |
| 5,702,386 A | 12/1997 | Stern et al. |
| 5,707,218 A | 1/1998 | Maher et al. |
| 5,707,336 A | 1/1998 | Rubin |
| 5,707,352 A | 1/1998 | Sekins et al. |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,727,569 A | 3/1998 | Benetti et al. |
| 5,728,094 A | 3/1998 | Edwards |
| 5,730,128 A | 3/1998 | Pomeranz et al. |
| 5,730,704 A | 3/1998 | Avitall |
| 5,730,726 A | 3/1998 | Klingenstein |
| 5,730,741 A | 3/1998 | Horzewski et al. |
| 5,735,846 A | 4/1998 | Panescu et al. |
| 5,740,808 A | 4/1998 | Panescu et al. |
| 5,741,248 A | 4/1998 | Stern et al. |
| 5,752,518 A | 5/1998 | McGee et al. |
| 5,755,714 A | 5/1998 | Murphy-Chutorian |
| 5,755,753 A | 5/1998 | Knowlton |
| 5,759,158 A | 6/1998 | Swanson |
| 5,765,568 A | 6/1998 | Sweezer et al. |
| 5,769,846 A | 6/1998 | Edwards et al. |
| 5,772,590 A | 6/1998 | Webster |
| 5,779,669 A | 7/1998 | Haissaguerre et al. |
| 5,779,698 A | 7/1998 | Clayman et al. |
| 5,782,239 A | 7/1998 | Webster |
| 5,782,797 A | 7/1998 | Schweich et al. |
| 5,782,827 A | 7/1998 | Gough et al. |
| 5,782,848 A | 7/1998 | Lennox |
| 5,782,899 A | 7/1998 | Imran |
| 5,792,064 A | 8/1998 | Panescu et al. |
| 5,795,303 A | 8/1998 | Swanson et al. |
| 5,800,375 A | 9/1998 | Sweezer et al. |
| 5,807,306 A | 9/1998 | Shapland et al. |
| 5,810,757 A | 9/1998 | Sweezer et al. |
| 5,810,807 A | 9/1998 | Ganz et al. |
| 5,817,028 A | 10/1998 | Anderson |
| 5,817,073 A | 10/1998 | Krespi |
| 5,820,554 A | 10/1998 | Davis et al. |
| 5,823,189 A | 10/1998 | Kordis |
| 5,827,277 A | 10/1998 | Edwards |
| 5,833,651 A | 11/1998 | Donovan et al. |
| 5,836,905 A | 11/1998 | Lemelson et al. |
| 5,836,947 A | 11/1998 | Fleischman et al. |
| 5,837,001 A | 11/1998 | Mackey |
| 5,843,075 A | 12/1998 | Taylor |
| 5,843,077 A | 12/1998 | Edwards |
| 5,846,238 A | 12/1998 | Jackson et al. |
| 5,848,969 A | 12/1998 | Panescu et al. |
| 5,848,972 A | 12/1998 | Triedman et al. |
| 5,849,026 A | 12/1998 | Zhou et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | Leveen et al. |
| 5,871,443 A | 2/1999 | Edwards et al. |
| 5,871,523 A | 2/1999 | Fleischman et al. |
| 5,873,852 A | 2/1999 | Vigil et al. |
| 5,873,865 A | 2/1999 | Horzewski et al. |
| 5,876,340 A | 3/1999 | Tu et al. |
| 5,876,399 A | 3/1999 | Chia et al. |
| 5,881,727 A | 3/1999 | Edwards |
| 5,882,346 A | 3/1999 | Pomeranz et al. |
| 5,891,135 A | 4/1999 | Jackson et al. |
| 5,891,136 A | 4/1999 | McGee et al. |
| 5,891,138 A | 4/1999 | Tu et al. |
| 5,893,847 A | 4/1999 | Kordis |
| 5,897,554 A | 4/1999 | Chia et al. |
| 5,899,882 A | 5/1999 | Waksman et al. |
| 5,904,651 A | 5/1999 | Swanson et al. |
| 5,904,711 A | 5/1999 | Flom et al. |
| 5,906,636 A | 5/1999 | Casscells, III et al. |
| 5,908,445 A | 6/1999 | Whayne et al. |
| 5,908,446 A | 6/1999 | Imran |
| 5,908,839 A | 6/1999 | Levitt et al. |
| 5,911,218 A | 6/1999 | DiMarco |
| 5,916,235 A | 6/1999 | Guglielmi |
| 5,919,147 A | 7/1999 | Jain |
| 5,919,172 A | 7/1999 | Golba |
| 5,924,424 A | 7/1999 | Stevens et al. |
| 5,928,228 A | 7/1999 | Kordis et al. |
| 5,931,835 A | 8/1999 | Mackey |
| 5,935,079 A | 8/1999 | Swanson et al. |
| 5,941,869 A | 8/1999 | Patterson et al. |
| 5,951,494 A | 9/1999 | Wang et al. |
| 5,951,546 A | 9/1999 | Lorentzen |
| 5,954,661 A | 9/1999 | Greenspon et al. |
| 5,954,662 A | 9/1999 | Swanson et al. |
| 5,954,717 A | 9/1999 | Behl et al. |
| 5,957,961 A | 9/1999 | Maguire et al. |
| 5,964,753 A | 10/1999 | Edwards |
| 5,964,796 A | 10/1999 | Imran |
| 5,971,983 A | 10/1999 | Lesh |
| 5,972,026 A | 10/1999 | Laufer et al. |
| 5,975,303 A | 11/1999 | Morell |
| 5,976,175 A | 11/1999 | Hirano et al. |

(56) References Cited

U.S. PATENT DOCUMENTS

| | | |
|---|---|---|
| 5,976,709 A | 11/1999 | Kageyama et al. |
| 5,979,456 A | 11/1999 | Magovern |
| 5,980,563 A | 11/1999 | Tu et al. |
| 5,984,917 A | 11/1999 | Fleischman et al. |
| 5,984,971 A | 11/1999 | Faccioli et al. |
| 5,991,650 A | 11/1999 | Swanson et al. |
| 5,992,419 A | 11/1999 | Sterzer et al. |
| 5,993,462 A | 11/1999 | Pomeranz et al. |
| 5,997,534 A | 12/1999 | Tu et al. |
| 5,999,855 A | 12/1999 | DiMarco |
| 6,001,054 A | 12/1999 | Regulla et al. |
| 6,003,517 A | 12/1999 | Sheffield et al. |
| 6,004,269 A | 12/1999 | Crowley et al. |
| 6,006,755 A | 12/1999 | Edwards |
| 6,008,211 A | 12/1999 | Robinson et al. |
| 6,009,877 A | 1/2000 | Edwards |
| 6,010,500 A | 1/2000 | Sherman et al. |
| 6,014,579 A | 1/2000 | Pomeranz et al. |
| 6,016,437 A | 1/2000 | Tu et al. |
| 6,023,638 A | 2/2000 | Swanson |
| 6,024,740 A | 2/2000 | Lesh et al. |
| 6,029,091 A | 2/2000 | De La Rama et al. |
| 6,033,397 A | 3/2000 | Laufer et al. |
| 6,036,687 A | 3/2000 | Laufer et al. |
| 6,036,689 A | 3/2000 | Tu et al. |
| 6,039,731 A | 3/2000 | Taylor et al. |
| 6,045,549 A | 4/2000 | Smethers et al. |
| 6,045,550 A | 4/2000 | Simpson et al. |
| 6,050,992 A | 4/2000 | Nichols |
| 6,053,172 A | 4/2000 | Hovda et al. |
| 6,053,909 A | 4/2000 | Shadduck |
| 6,056,744 A | 5/2000 | Edwards |
| 6,056,769 A | 5/2000 | Epstein et al. |
| 6,063,078 A | 5/2000 | Wittkampf |
| 6,071,280 A | 6/2000 | Edwards et al. |
| 6,071,282 A | 6/2000 | Fleischman |
| 6,083,255 A | 7/2000 | Laufer et al. |
| 6,090,104 A | 7/2000 | Webster |
| 6,092,528 A | 7/2000 | Edwards |
| 6,102,886 A | 8/2000 | Lundquist et al. |
| 6,106,524 A | 8/2000 | Eggers et al. |
| 6,123,702 A | 9/2000 | Swanson et al. |
| 6,123,703 A | 9/2000 | Tu et al. |
| 6,139,527 A | 10/2000 | Laufer et al. |
| 6,139,571 A | 10/2000 | Fuller et al. |
| 6,142,993 A | 11/2000 | Whayne et al. |
| 6,143,013 A | 11/2000 | Samson et al. |
| 6,149,647 A | 11/2000 | Tu et al. |
| 6,152,143 A | 11/2000 | Edwards |
| 6,152,899 A | 11/2000 | Farley et al. |
| 6,159,194 A | 12/2000 | Eggers et al. |
| 6,165,169 A | 12/2000 | Panescu et al. |
| 6,179,833 B1 | 1/2001 | Taylor |
| 6,183,468 B1 | 2/2001 | Swanson et al. |
| 6,198,970 B1 | 3/2001 | Freed et al. |
| 6,200,311 B1 | 3/2001 | Danek et al. |
| 6,200,332 B1 | 3/2001 | Del Giglio |
| 6,200,333 B1 | 3/2001 | Laufer |
| 6,210,367 B1 | 4/2001 | Carr |
| 6,212,433 B1 | 4/2001 | Behl |
| 6,214,002 B1 | 4/2001 | Fleischman et al. |
| 6,216,043 B1 | 4/2001 | Swanson et al. |
| 6,216,044 B1 | 4/2001 | Kordis |
| 6,217,576 B1 | 4/2001 | Tu et al. |
| 6,235,024 B1 | 5/2001 | Tu |
| 6,241,727 B1 | 6/2001 | Tu et al. |
| 6,245,065 B1 | 6/2001 | Panescu et al. |
| 6,254,598 B1 | 7/2001 | Edwards et al. |
| 6,258,087 B1 | 7/2001 | Edwards et al. |
| 6,264,653 B1 | 7/2001 | Falwell |
| 6,269,813 B1 | 8/2001 | Fitzgerald et al. |
| 6,270,476 B1 | 8/2001 | Santoianni et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,304 B1 | 9/2001 | Eggers et al. |
| 6,296,639 B1 | 10/2001 | Truckai et al. |
| 6,299,633 B1 | 10/2001 | Laufer |
| 6,319,251 B1 | 11/2001 | Tu et al. |
| 6,322,559 B1 | 11/2001 | Daulton et al. |
| 6,322,584 B2 | 11/2001 | Ingle et al. |
| 6,338,727 B1 | 1/2002 | Noda et al. |
| 6,338,836 B1 | 1/2002 | Kuth et al. |
| 6,346,104 B2 | 2/2002 | Daly et al. |
| 6,355,031 B1 | 3/2002 | Edwards et al. |
| 6,379,352 B1 | 4/2002 | Reynolds et al. |
| 6,416,511 B1 | 7/2002 | Lesh et al. |
| 6,416,740 B1 | 7/2002 | Unger |
| 6,423,105 B1 | 7/2002 | Iijima et al. |
| 6,425,895 B1 | 7/2002 | Swanson et al. |
| 6,440,129 B1 | 8/2002 | Simpson |
| 6,442,435 B2 | 8/2002 | King et al. |
| 6,454,775 B1 | 9/2002 | Demarais et al. |
| 6,458,121 B1 | 10/2002 | Rosenstock et al. |
| 6,460,545 B2 | 10/2002 | Kordis |
| 6,488,673 B1 | 12/2002 | Laufer et al. |
| 6,488,679 B1 | 12/2002 | Swanson et al. |
| 6,493,589 B1 | 12/2002 | Medhkour et al. |
| 6,494,880 B1 | 12/2002 | Swanson et al. |
| 6,496,738 B2 | 12/2002 | Carr |
| 6,514,246 B1 | 2/2003 | Swanson et al. |
| 6,526,320 B2 | 2/2003 | Mitchell |
| 6,529,756 B1 | 3/2003 | Phan et al. |
| 6,544,226 B1 | 4/2003 | Gaiser et al. |
| 6,544,262 B2 | 4/2003 | Fleischman |
| 6,547,788 B1 | 4/2003 | Maguire et al. |
| 6,558,378 B2 | 5/2003 | Sherman et al. |
| 6,572,612 B2 | 6/2003 | Stewart et al. |
| 6,575,623 B2 | 6/2003 | Werneth |
| 6,575,969 B1 | 6/2003 | Rittman, III et al. |
| 6,582,427 B1 | 6/2003 | Goble et al. |
| 6,582,430 B2 | 6/2003 | Hall |
| 6,589,235 B2 | 7/2003 | Wong et al. |
| 6,610,054 B1 | 8/2003 | Edwards et al. |
| 6,620,159 B2 | 9/2003 | Hegde |
| 6,626,903 B2 | 9/2003 | McGuckin et al. |
| 6,635,056 B2 | 10/2003 | Kadhiresan et al. |
| 6,638,273 B1 | 10/2003 | Farley et al. |
| 6,640,120 B1 | 10/2003 | Swanson et al. |
| 6,645,200 B1 | 11/2003 | Koblish et al. |
| 6,652,548 B2 | 11/2003 | Evans et al. |
| 6,669,693 B2 | 12/2003 | Friedman |
| 6,673,068 B1 | 1/2004 | Berube |
| 6,692,492 B2 | 2/2004 | Simpson et al. |
| 6,699,243 B2 | 3/2004 | West et al. |
| 6,714,822 B2 | 3/2004 | King et al. |
| 6,723,091 B2 | 4/2004 | Goble et al. |
| 6,743,197 B1 | 6/2004 | Edwards |
| 6,749,604 B1 | 6/2004 | Eggers et al. |
| 6,749,606 B2 | 6/2004 | Keast et al. |
| 6,767,347 B2 | 7/2004 | Sharkey et al. |
| 6,770,070 B1 | 8/2004 | Balbierz |
| 6,802,843 B2 | 10/2004 | Truckai et al. |
| 6,805,131 B2 | 10/2004 | Kordis |
| 6,837,888 B2 | 1/2005 | Ciarrocca et al. |
| 6,840,243 B2 | 1/2005 | Deem et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,866,662 B2 | 3/2005 | Fuimaono et al. |
| 6,881,213 B2 | 4/2005 | Ryan et al. |
| 6,893,436 B2 | 5/2005 | Woodard et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,917,834 B2 | 7/2005 | Koblish et al. |
| 6,939,346 B2 | 9/2005 | Kannenberg et al. |
| 6,954,977 B2 | 10/2005 | Maguire et al. |
| 7,027,869 B2 | 4/2006 | Danek et al. |
| 7,043,307 B1 | 5/2006 | Zelickson et al. |
| 7,104,987 B2 | 9/2006 | Biggs et al. |
| 7,104,990 B2 | 9/2006 | Jenkins et al. |
| 7,118,568 B2 | 10/2006 | Hassett et al. |
| 7,122,033 B2 | 10/2006 | Wood |

(56) References Cited

U.S. PATENT DOCUMENTS

| | | | |
|---|---|---|---|
| 7,131,445 B2 | 11/2006 | Amoah | |
| 7,186,251 B2 | 3/2007 | Malecki et al. | |
| 7,198,635 B2 | 4/2007 | Danek et al. | |
| 7,200,445 B1 | 4/2007 | Dalbec et al. | |
| 7,241,295 B2 | 7/2007 | Maguire | |
| 7,255,693 B1 | 8/2007 | Johnston et al. | |
| 7,266,414 B2 | 9/2007 | Cornelius et al. | |
| 7,273,055 B2 | 9/2007 | Danek et al. | |
| 7,357,770 B1 | 4/2008 | Cutrer et al. | |
| 7,425,212 B1 | 9/2008 | Danek et al. | |
| 7,542,802 B2 | 6/2009 | Biggs et al. | |
| 7,556,624 B2 | 7/2009 | Laufer et al. | |
| 7,740,017 B2 | 6/2010 | Danek et al. | |
| 8,161,978 B2 | 4/2012 | Danek et al. | |
| 8,584,681 B2 | 11/2013 | Dakek et al. | |
| 2003/0050631 A1 | 3/2003 | Mody et al. | |
| 2003/0065371 A1 | 4/2003 | Satake | |
| 2003/0069570 A1 | 4/2003 | Witzel et al. | |
| 2003/0187430 A1 | 10/2003 | Vorisek | |
| 2003/0236455 A1 | 12/2003 | Swanson et al. | |
| 2004/0153056 A1 | 8/2004 | Muller et al. | |
| 2004/0249401 A1 | 12/2004 | Rabiner et al. | |
| 2005/0010270 A1 | 1/2005 | Laufer | |
| 2005/0096644 A1 | 5/2005 | Hall et al. | |
| 2005/0096647 A1 | 5/2005 | Steinke et al. | |
| 2005/0171396 A1 | 8/2005 | Pankratov et al. | |
| 2005/0193279 A1 | 9/2005 | Daners | |
| 2005/0240176 A1 | 10/2005 | Oral et al. | |
| 2005/0251128 A1 | 11/2005 | Amoah | |
| 2006/0062808 A1 | 3/2006 | Laufer et al. | |
| 2006/0079887 A1 | 4/2006 | Buysse et al. | |
| 2006/0089637 A1 | 4/2006 | Werneth et al. | |
| 2006/0135953 A1 | 6/2006 | Kania et al. | |
| 2006/0137698 A1 | 6/2006 | Danek et al. | |
| 2006/0247617 A1 | 11/2006 | Danek et al. | |
| 2006/0247618 A1 | 11/2006 | Kaplan et al. | |
| 2006/0247619 A1 | 11/2006 | Kaplan et al. | |
| 2006/0247726 A1 | 11/2006 | Biggs et al. | |
| 2006/0247727 A1 | 11/2006 | Biggs et al. | |
| 2006/0247746 A1 | 11/2006 | Danek et al. | |
| 2006/0282071 A1 | 12/2006 | Utley et al. | |
| 2007/0074719 A1 | 4/2007 | Danek et al. | |
| 2007/0083194 A1 | 4/2007 | Kunis et al. | |
| 2007/0083197 A1 | 4/2007 | Danek et al. | |
| 2007/0100390 A1 | 5/2007 | Danaek et al. | |
| 2007/0106108 A1 | 5/2007 | Hermann et al. | |
| 2007/0106292 A1* | 5/2007 | Kaplan | A61F 7/123 606/41 |
| 2007/0106296 A1 | 5/2007 | Laufer et al. | |
| 2007/0106348 A1 | 5/2007 | Laufer | |
| 2007/0118184 A1 | 5/2007 | Danek et al. | |
| 2007/0118190 A1 | 5/2007 | Danek et al. | |
| 2007/0123958 A1 | 5/2007 | Laufer | |
| 2007/0123961 A1 | 5/2007 | Danek et al. | |
| 2007/0129720 A1 | 6/2007 | Demarais et al. | |
| 2008/0004596 A1 | 1/2008 | Yun et al. | |
| 2008/0125772 A1 | 5/2008 | Stone et al. | |
| 2008/0255642 A1 | 10/2008 | Zarins et al. | |
| 2008/0269539 A1 | 10/2008 | Cutrer et al. | |
| 2009/0030477 A1 | 1/2009 | Jarrard | |
| 2009/0043301 A1 | 2/2009 | Jarrard et al. | |
| 2009/0069797 A1 | 3/2009 | Danek et al. | |
| 2009/0112203 A1 | 4/2009 | Danek et al. | |
| 2009/0143705 A1 | 6/2009 | Danek et al. | |
| 2009/0143776 A1 | 6/2009 | Danek et al. | |
| 2009/0192505 A1 | 7/2009 | Askew et al. | |
| 2009/0192508 A1 | 7/2009 | Laufer et al. | |
| 2009/0306644 A1 | 12/2009 | Mayse et al. | |
| 2011/0106074 A1 | 5/2011 | Kunis et al. | |
| 2011/0118726 A1 | 5/2011 | De La Rama et al. | |
| 2012/0157989 A1* | 6/2012 | Stone | A61B 18/1492 606/41 |
| 2013/0218158 A1 | 8/2013 | Danek et al. | |

FOREIGN PATENT DOCUMENTS

| | | |
|---|---|---|
| DE | 19529634 A1 | 2/1997 |
| EP | 0189329 A2 | 7/1986 |
| EP | 189329 A3 | 6/1987 |
| EP | 0282225 A2 | 9/1988 |
| EP | 286145 A2 | 10/1988 |
| EP | 280225 A3 | 3/1989 |
| EP | 286145 A3 | 10/1990 |
| EP | 282225 B1 | 6/1992 |
| EP | 0499491 A2 | 8/1992 |
| EP | 0768091 A1 | 4/1997 |
| EP | 0908150 A1 | 4/1999 |
| EP | 908713 A1 | 4/1999 |
| EP | 908150 B1 | 5/2003 |
| EP | 768091 B1 | 7/2003 |
| EP | 1297795 B1 | 8/2005 |
| FR | 2659240 A1 | 9/1991 |
| GB | 2233293 A | 1/1991 |
| GB | 2233293 B | 2/1994 |
| JP | 56128571 A | 10/1981 |
| JP | 59167707 A2 | 9/1984 |
| JP | 7289557 A | 11/1995 |
| JP | 9047518 A2 | 2/1997 |
| JP | 9243837 A2 | 9/1997 |
| JP | 10026709 A2 | 1/1998 |
| JP | 2002-536107 A | 10/2002 |
| JP | 2002-537889 A | 11/2002 |
| JP | 2009-515603 A | 4/2009 |
| JP | 2011-507656 A | 3/2011 |
| JP | 2011-507656 A | 3/2011 |
| JP | 2011-115603 A | 6/2011 |
| JP | 2012-508635 A | 4/2012 |
| JP | 2013-510689 A | 3/2013 |
| RU | 2053814 C1 | 2/1996 |
| RU | 2091054 C1 | 9/1997 |
| SU | 545358 T | 2/1977 |
| WO | WO-1989011311 A1 | 11/1989 |
| WO | WO-1995002370 A2 | 1/1995 |
| WO | WO-1995010322 A1 | 4/1995 |
| WO | WO-1996004860 A1 | 2/1996 |
| WO | WO-1996010961 A1 | 4/1996 |
| WO | WO-1997032532 A1 | 9/1997 |
| WO | WO-1997033715 A1 | 9/1997 |
| WO | WO-1997037715 A1 | 10/1997 |
| WO | WO-9740751 A1 | 11/1997 |
| WO | WO-1998044854 A1 | 10/1998 |
| WO | WO-1998052480 A1 | 11/1998 |
| WO | WO-9856234 A1 | 12/1998 |
| WO | WO-9858681 A2 | 12/1998 |
| WO | WO-1998056324 A1 | 12/1998 |
| WO | WO-1999003413 A1 | 1/1999 |
| WO | WO-1998058681 A3 | 3/1999 |
| WO | WO-1999013779 A2 | 3/1999 |
| WO | WO-9913779 A3 | 5/1999 |
| WO | WO-9932040 A1 | 7/1999 |
| WO | WO-1999034741 A1 | 7/1999 |
| WO | WO-1999044506 A1 | 9/1999 |
| WO | WO-1999045855 A1 | 9/1999 |
| WO | WO-9964109 A1 | 12/1999 |
| WO | WO-2000051510 A1 | 9/2000 |
| WO | WO-0062699 A2 | 10/2000 |
| WO | WO-0062699 A3 | 10/2000 |
| WO | WO-2001003642 A1 | 1/2001 |
| WO | WO-0232333 A1 | 4/2002 |
| WO | WO-0232334 A1 | 4/2002 |
| WO | WO-2008049084 A2 | 4/2008 |
| WO | WO-2009082433 A2 | 7/2009 |
| WO | WO-2009137819 A1 | 11/2009 |

OTHER PUBLICATIONS

Bel E.H., ""Hot stuff": Bronchial Thermoplasty for Asthma," American Journal of Respiratory and Critical Care Medicine, 2006, 173 (9), 941-943.

Brown R.H., et al., "Effect of Bronchial Thermoplasty on Airway Distensibility," European Respiratory Journal, 2005, 26 (2), 277-282.

(56) References Cited

OTHER PUBLICATIONS

Brown R.H., et al., "In Vivo evaluation of the Effectiveness of Bronchial Thermoplasty with Computed Tomography," Journal of Applied Physiology, 2005, 98 (5), 1603-1606.
Chhajed P.N., et al., "Will there be a Role for Bronchoscopic Radiofrequency Ablation", Journal of Bronchology, 2005, 12 (3), 184-186.
Abandoned U.S. Appl. No. 09/095,323, filed Jun. 10, 1998.
Abandoned U.S. Appl. No. 09/244,173, filed Feb. 4, 1999.
Co-pending U.S. Appl. No. 12/640,644, filed Dec. 17, 2009.
U.S. Appl. No. 12/727,156, filed Mar. 18, 2010.
U.S. Appl. No. 12/765,704, filed Apr. 22, 2010.
Cox G., et al., "Asthma Control during the Year after Bronchial Thermoplasty," New England journal of medicine, 2007, 356 (13), 1327-1337.
Cox G., et al., "Asthma Intervention Research (AIR) Trial Evaluating Bronchial Thermoplasty: Early Results," American Thoracic Society Annual Meeting, 2002, 1 page.
Cox G., et al., "Bronchial Thermoplasty for Asthma," American Journal of Respiratory and Critical Care Medicine, 2006, 173 (9), 965-969.
Cox G., et al., "Bronchial Thermoplasty: Long-Term Follow-Up and Patient Satisfaction," Chest, 2004, 126 (4), 822s.
Cox G., et al., "Bronchial Thermoplasty: One-Year Update, American Thoracic Society Annual Meeting," American Journal of Respiratory and Critical Care Medicine, 2004, 169, A313.
Cox G., et al., "Clinical Experience with Bronchial Thermoplasty for the Treatment of Asthma," Chest, 2003, 124, 106S.
Cox G., et al., "Development of a Novel Bronchoscopic Therapy for Asthma," Journal of Allergy and Clinical Immunology, 2003, 113 (2), S33.
Cox G., et al., "Early Clinical Experience with Bronchial Thermoplasty for the Treatment of Asthma," American Thoracic Society Annual Meeting, 2002, 1068.
Cox G., et al., "Impact of Bronchial Thermoplasty on Asthma Status: Interim Results from the AIR Trial," 2006, 1 page.
Cox G., et al., "Radiofrequency Ablation of Airway Smooth Muscle for Sustained Treatment of Asthma: Preliminary Investigations," European Respiratory Journal, 2004, 24 (4), 659-663.
Danek C.J., et al., "Bronchial Thermoplasty Reduces Canine Airway Responsiveness to Local Methacholine Challenge," American Thoracic Society Annual Meeting, 2002, 1 page.
Danek C.J., et al., "Reduction in Airway Hyperresponsiveness to Methacholine by the Application of RF Energy in Dogs," Journal of Applied Physiology, 2004, 97 (5), 1946-1953.
Dierkesmann R., "Indication and Results of Endobronchial Laser Therapy," Lung, 1990, 168, 1095-1102.
Global Strategy for Asthma Management and Prevention, National Institute of Health, National Heart, Lung and Blood Institute, 2002, 192 pages.
Hogg J. C., "The Pathology of Asthma," APMIS, 1997, 105 (10), 735-745.
International Search Report for Application No. PCT/US00/05412, dated Jun. 20, 2000, 2 pages.
International Search Report for Application No. PCT/US00/18197, dated Oct. 3, 2000, 1 page.
International Search Report for Application No. PCT/US00/28745, dated Mar. 28, 2001, 6 pages.
International Search Report for Application No. PCT/US01/32321, dated Jan. 18, 2002, 2 pages.
International Search Report for Application No. PCT/US98/03759, dated Jul. 30, 1998, 1 page.
International Search Report for Application No. PCT/US98/26227, dated Mar. 25, 1999, 1 page.
International Search Report for Application No. PCT/US99/00232, dated Mar. 4, 1999, 1 page.
International Search Report for Application No. PCT/US99/12986, dated Sep. 29, 1999, 1 page.
Ivanyuta O.M., et al., "Effect of Low-Power Laser Irradiation of Bronchial Mucosa on the State of Systemic and Local Immunity in Patients with Chronic Bronchitis," Problemy Tuberkuleza, 1991, 6, 26-29.
James A.L., et al., "The Mechanics of Airway Narrowing in Asthma," American Review of Respiratory Diseases, 1989, 139 (1), 242-246.
Janssen L.J., "Asthma Therapy: How far have we Come, Why did we Fail and Where should we go Next", European Respiratory Journal, 2009, 33 (1), 11-20.
Jeffery P.K, "Remodeling in Asthma and Chronic Obstructive Lung Disease," American Journal of Respiratory and Critical Care Medicine, 2001, 164 (10), S28-S38.
Johnson S. R., et al., "Synthetic Functions of Airway Smooth Muscle in Asthma," Trends Pharmacol. Sci., 1997, 18 (8), 288-292.
Kitamura S., "Color Atlas of Clinical Application of Fiberoptic Bronchoscopy," 1990, Year Book Medical Publishers, 2 pages.
Kraft M., "The Distal Airways: Are they Important in Asthma", European Respiratory Journal, 1999, 14 (6), 1403-1417.
Laviolette M., et al., "Asthma Intervention Research (Air) Trial: Early Safety Assessment of Bronchial Thermoplasty," American Journal of Respiratory and Critical Care Medicine, 2004, 169, A314.
Leff A., et al., "Bronchial Thermoplasty Alters Airway Smooth Muscle and Reduces Responsiveness in Dogs: A Possible Procedure for the Treatment of Asthma," American Thoracic Society Annual Meeting, 2002, 1 page.
Lim E.C., et al., "Botulinum Toxin: A Novel Therapeutic Option for Bronchial Asthma", Medical Hypotheses, 2006, 66 (5), 915-919.
Lombard C.M., et al., "Histologic Effects of Bronchial Thermoplasty of Canine and Human Airways,"American Thoracic Society Annual Meeting, 2002, 1 page.
Macklem P. T., "Mechanical Factors Determining Maximum Bronchoconstriction," European Respiratory Journal, 1989, 6, 516s-519s.
Mayse M.L., et al., "Clinical Pearls for Bronchial Thermoplasty," Journal of Bronchology, 2007, 14 (2), 115-123.
Miller J.D., et al., "A Prospective Feasibility Study of Bronchial Thermoplasty in the Human Airway," Chest, 2005, 127 (6), 1999-2006.
Miller J.D., et al., "Bronchial Thermoplasty is Well Tolerated by Non-Asthmatic Patients Requiring Lobectomy," American Thoracic Society Annual Meeting, 2002, 1 page.
Mitzner W., "Airway Smooth Muscle the Appendix of the Lung," American Journal of Respiratory and Critical Care Medicine, 2004, 169 (7), 787-790.
Mitzner W., "Bronchial Thermoplasty in Asthma," Allergology International, 2006, 55 (3), 225-234.
Netter F.H., "Respiratory System: A Compilation of Paintings Depicting Anatomy and Embryology, Physiology, Pathology, Pathophysiology, and Clinical Features and Treatment of Diseases,In the CIBA Collection of Medical Illustrations M.B. Divertie, ed., Summit: New Jerse," 1979, 7, 119-135.
Notice of final Rejection, Japanese Patent Application No. 2000-553172, dated Sep. 2, 2008, 5 pages.
Provotorov V.M., et al., "The Clinical Efficacy of Treating Patients with Nonspecific Lung Diseases Using Low-energy Laser Irradiation and Intrapulmonary Drug Administration," Terapevticheskii Arkhiv, 1991, 62 (12), 18-23.
Rubin A., et al., "Bronchial Thermoplasty Improves Asthma Status of Moderate to Severe Perissent Asthmatics Over and Above Current Standard-of-Care," American College of Chest Physicians, 2006, 2 pages.
Seow C.Y., et al., "Historical Perspective on Airway Smooth Muscle: The Saga of a Frustrated Cell," Journal of Applied Physiology, 2001, 91 (2), 938-952.
Shesterina M.V., et al., "Effect of Laser Therapy on Immunity in Patients with Bronchial Asthma and Pulmonary Tuberculosis," Problemy Tuberkuleza, 1994, 5, 23-26.
Shore S.A., "Airway Smooth Muscle in Asthma—Not Just More of the Same," New England Journal of Medicine, 2004, 351 (6), 531-532.

(56) References Cited

OTHER PUBLICATIONS

Solway J., et al., "Airway Smooth Muscle as a Target for Asthma Therapy," New England Journal of medicine, 2007, 356 (13), 1367-1369.

Sterk P.J., et al., "Heterogeneity of Airway Hyperresponsiveness: Time for Unconventional, But Traditional, Studies," Journal of Applied Physiology, 2004, 96 (6), 2017-2018.

Toma T.P., et al., "Brave New World for Interventional Bronchoscopy," Thorax, 2005, 60 (3), 180-181.

Trow T.K., "Clinical Year in Review I: Diagnostic Imaging, Asthma, Lung Transplantation, and Interventional Pulmonology," Proceedings of the American Thoracic Society, 2006, 3 (7), 553-556.

UNSW Embryo-Respiratory System [online], Embryology, 2007, [retrieved on Dec. 10, 2007]. Retrieved from the internet: (URL:http://embryology.med.unsw.edu.au/Refer/respire/sclect.htm).

Vasilotta P.L., et al., "I-R Laser: A New Therapy in Rhino-Sino-Nasal Bronchial Syndrome with Asthmatic Component," American Society for Laser Medicine and Surgery Abstracts, 74. 1993.

Vorotnev A.I., et al., "The Treatment of Patients with Chronic Obstructive Bronchitis by Using a Low-power Laser at a General Rehabilitation Center," Terapevticheskii Arkhiv, 1997, 69 (3), 17-19.

Wiggs B.R., et al., "On the Mechanism of Mucosal Folding in Normal and Asthmatic Airways," Journal of Applied Physiology, 1997, 83 (6), 1814-1821.

Wilson S.R., et al., "Global Assessment after Bronchial Thermoplasty: The Patients Perspective," Journal of Outcomes Research, 2006, 10, 37-46.

Wizeman W., et al., "A Computer Model of Thermal Treatment of Airways by Radiofrequency (RF) Energy Delivery," American Thoracic Society Annual Meeting, 2007, 1 page.

U.S. Appl. No. 09/436,455, filed Nov. 8, 1999.

International Search Report for Application No. PCT/US2014/050204, dated Oct. 24, 2014, 5 pages.

\* cited by examiner

EXPANDABLE CATHETER AND RELATED METHODS OF MANUFACTURE AND USE

CROSS-REFERENCE TO RELATED APPLICATION

This application is a continuation of U.S. application Ser. No. 14/454,383, filed Aug. 7, 2014, which claims the benefit of U.S. Provisional Application No. 61/864,292, filed Aug. 9, 2013, the disclosures of which are incorporated herein by reference in their entireties.

FIELD

Examples of the present disclosure relate generally to medical devices, and methods for manufacturing and using these medical devices. In particular, examples of the present disclosure relate to catheters and methods for manufacturing and using catheters for applying energy to tissue (e.g., airway passageways in a lung) in a minimally invasive procedure.

BACKGROUND OF THE INVENTION

Chronic obstructive pulmonary disease (COPD) includes conditions such as, e.g., chronic bronchitis and emphysema. COPD currently affects over 15 million people in the United States alone and is currently the third leading cause of death in the country. The primary cause of COPD is the inhalation of cigarette smoke, responsible for over 90% of COPD cases. The economic and social burden of the disease is substantial and is increasing.

Chronic bronchitis is characterized by chronic cough with sputum production. Due to airway inflammation, mucus hypersecretion, airway hyper-responsiveness, and eventual fibrosis of the airway walls, significant airflow and gas exchange limitations result.

Emphysema is characterized by the destruction or damage of the lung parenchyma. This destruction of the lung parenchyma leads to a loss of elastic recoil and tethering which maintains airway patency. Because bronchioles are not supported by cartilage like the larger airways, they have little intrinsic support and therefore are susceptible to collapse when destruction of tethering occurs, particularly during exhalation.

Acute exacerbations of COPD (AECOPD) often require emergency care and inpatient hospital care. An AECOPD is defined by a sudden worsening of symptoms (e.g., increase in or onset of cough, wheeze, and sputum changes) that typically last for several days, but can persist for weeks. An AECOPD is typically triggered by a bacterial infection, viral infection, or pollutants, which manifest quickly into airway inflammation, mucus hypersecretion, and bronchoconstriction, causing significant airway restriction.

Despite relatively efficacious drugs (e.g., long-acting muscarinic antagonists, long-acting beta agonists, corticosteroids, and antibiotics) that treat COPD symptoms, a particular segment of patients known as "frequent exacerbators" often visit the emergency room and hospital with exacerbations. These patients also have a more rapid decline in lung function, poorer quality of life, and a greater mortality risk.

Reversible obstructive pulmonary disease includes asthma and reversible aspects of COPD. Asthma is a disease in which bronchoconstriction, excessive mucus production, and inflammation and swelling of airways occur, causing widespread but variable airflow obstruction thereby making it difficult for the asthma sufferer to breathe. Asthma is further characterized by acute episodes of airway narrowing via contraction of hyper-responsive airway smooth muscle.

The reversible aspects of COPD include excessive mucus production and partial airway occlusion, airway narrowing secondary to smooth muscle contraction, and bronchial wall edema and inflation of the airways. Usually, there is a general increase in bulk (hypertrophy) of the large bronchi and chronic inflammatory changes in the small airways. Excessive amounts of mucus are found in the airways, and semisolid plugs of mucus may occlude some small bronchi. Also, the small airways are narrowed and show inflammatory changes.

In asthma, chronic inflammatory processes in the airway play a central role in increasing the resistance to airflow within the lungs. Many cells and cellular elements are involved in the inflammatory process including, but not limited to, mast cells, eosinophils, T lymphocytes, neutrophils, epithelial cells, and even airway smooth muscle itself. The reactions of these cells result in an associated increase in sensitivity and hyperresponsiveness of the airway smooth muscle cells lining the airways to particular stimuli.

The chronic nature of asthma can also lead to remodeling of the airway wall (e.g., structural changes such as airway wall thickening or chronic edema) that can further affect the function of the airway wall and influence airway hyper-responsiveness. Epithelial denudation exposes the underlying tissue to substances that would not normally otherwise contact the underlying tissue, further reinforcing the cycle of cellular damage and inflammatory response.

In susceptible individuals, asthma symptoms include recurrent episodes of shortness of breath (dyspnea), wheezing, chest tightness, and cough, Currently, asthma is managed by a combination of stimulus avoidance and pharmacology.

Bronchiectasis is a condition where lung airways become enlarged, flabby, and/or scarred. In the injured areas, mucus often builds up, causing obstruction and/or infections. A cycle of repeated infections may continue to damage the airways and cause greater mucus build-up. Bronchiectasis can lead to health problems such as respiratory failure, atelectasis, and heart failure.

Strategies for managing COPD and other conditions of the lung include smoking cessation, vaccination, rehabilitation, and drug treatments (e.g., inhalers or oral medication). Drug treatments of COPD conditions, such as, e.g., mucus production, inflammation, and bronchoconstriction often suffer from poor patient compliance. That is, certain patients may not accurately administer prescribed doses, reducing the efficacy of treatment. For drug treatments utilizing inhalation, there is also an accompanying drug loss due to upper airway entrapment, which may lead to an overprescription of active drugs. Also, inhalation treatments can be ineffective at treating smaller airways of the lung (e.g., airways that are smaller than 2 mm). For drug treatments utilizing oral administration, there is an accompanying systemic loss which also leads to an over-prescription of active drugs. The over-prescription of drugs may result in suboptimal treatment and/or a build-up of toxins within the lungs and/or other organ systems. In other situations, drugs may not be deposited evenly to areas of the lungs because of particle size and/or blockage of airways preventing the drugs from reaching distal regions of the lungs (e.g., a heterogeneous delivery of drugs). Blockages may be caused by mucus and narrowing of the airway due to inflammation and remodelling.

The use of radiofrequency (RF) energy in medical applications is rapidly increasing. RF energy can be used to treat a variety of conditions affecting numerous body systems, such as, e.g., the respiratory system, the circulatory system, the digestive system, the immune system, the muscular system, among others. Various non-drug energy delivery procedures for, among other things, treatment of COPD, such as, e.g., severe persistent asthma, for which inhaled corticosteroids and long-acting beta-agonists are an insufficient treatment. In order to apply the energy delivery procedures, a catheter may be positioned to deliver thermal energy to a body lumen, such as a lung airway wall, for reducing excessive airway smooth muscle (ASM), and clear the air pathway within the trachea or lungs of a patient. The catheter may include an electrode array at a distal portion, which may be manually expanded to position the electrode array in communication with the airway wall. The electrode array may be coupled to one or more thermocouple wires for determining temperature of the electrode array to control the thermal energy delivered to the airway wall.

Conventionally, the electrode array can include elongated electrodes, which are welded together and coupled to hypotubes at their distal and proximal ends. Since the electrode array and the hypotubes are conductive to each other, welding of the electrode array only allows for monopolar design of delivering electrical energy to the electrode array. Moreover, in conventional arrangements, less space is available for the thermocouple wire to extend proximally through a proximal hypotube attached to the electrode array due to welding of the electrode array.

Therefore, there exists a need for an improved catheter design that permits different configurations (including, e.g., monopolar or bipolar configurations) for the delivery of electrical energy to body lumens, and increases effective space available for, among other things, thermocouple wire attachment. The improved catheter designs would also reduce the number of steps needed to assemble and/or manufacture the electrode array by, e.g., eliminating the need for welding together multiple electrodes of the electrode array. In other examples, there exists a need for other improvements. For example, certain electrode arrays, e.g., monopolar electrode arrays, may create uneven heating distribution, and may concentrate heating in the regions surrounding the electrodes to undesirable levels.

SUMMARY OF THE INVENTION

In one example, a medical device may include an expandable electrode assembly reciprocally movable between a first configuration and a second configuration. The expandable electrode assembly may include a first plurality of longitudinally extending legs formed in a first partially tubular member, a second plurality of longitudinally extending legs formed in a second partially tubular member, a first end piece formed by first ends of the first and second partially tubular members, and a second end piece formed by second ends of the first and second partially tubular members, wherein a portion of the second partially tubular member is configured to be received in a portion of the first partially tubular member.

Various examples of the medical device may include one or more of the following features: legs of first partially tubular member circumferentially alternate with legs of the second partially tubular member; the first ends of the first and second partially tubular members are substantially C-shaped or other shapes that are capable of being coupled, and the first end piece is formed by inserting the first end of the second partially tubular member into a volume partially defined by the first end of the first partially tubular member; when a portion of the second partially tubular member is received in a portion of the first partially tubular member, the first and second plurality of longitudinally extending legs define an expandable electrode array, such as a basket; the second end piece further includes an offset that extends longitudinally beyond the first end piece; an activation element disposed through first and second end pieces, the activation element configured to move the plurality of legs radially outward from the first configuration to the second configuration, and reciprocally back to the first configuration or the legs can have a shape memory effect that restores the legs to the first configuration; the activation element is electrically conductive and configured to deliver electrical energy to at least one of the first and second plurality of longitudinally extending legs; each of the first and second plurality of longitudinally extending legs includes: a first insulated section; a second insulated section, and an exposed electrically conductive section between the first and second insulated sections; the first and second end pieces are insulated; the second end of the second partially tubular member includes a circumferentially extending gap between first and second C-shaped portions, at least one of the second plurality of longitudinally extending legs extends from the first C-shaped portion, and at least one of the second plurality of longitudinally extending legs extends from the second C-shaped portion; the first end of the first partially tubular member includes a circumferentially extending gap between first and second C-shaped portions; at least one of the first plurality of longitudinally extending legs extends from the first C-shaped portion of the first partially tubular member, and at least one of the first plurality of longitudinally extending legs extends from the second C-shaped portion of the first partially tubular member; the first end piece further includes a first longitudinally extending gap disposed between circumferential ends of the first end piece, and the second end piece further includes a second longitudinally extending gap disposed between circumferential ends of the second end piece; a tube disposed around at least one leg of the first or second plurality of legs; a third longitudinally extending gap disposed in either first or second end of the first partially tubular member, the tube extending through the third longitudinally extending gap when the basket is in an expanded configuration; an endcap disposed through the first or second longitudinally extending gap, the endcap configured to prevent rotation of the first partially tubular member relative to the second partially tubular member.

In another example, a medical device may include a first partially tubular member having a first end, a second end, a first plurality of legs extending between the first and second ends of the first partially tubular member. The medical device may include a second partially tubular member including a first end, a second end, and a second plurality of legs extending between the first and second ends of the second partially tubular member, wherein the first ends of the first and second partially tubular members are coupled together, the second ends of the first and second partially tubular members are coupled together, and the first and second plurality of legs are disposed about a longitudinal axis of the medical device.

Various examples of the medical device may include one or more of the following features: legs of first partially tubular member circumferentially alternate with legs of the second partially tubular member; and the first and second ends of the first and second partially tubular members are C-shaped.

In another example, a method of delivering energy to a body lumen using a medical device may include inserting the medical device into the body lumen. The medical device may include a basket reciprocally movable between a collapsed configuration and an expanded configuration. The basket may include a first plurality of longitudinally extending legs formed in a first partially tubular member, a second plurality of longitudinally extending legs formed in a second partially tubular member, a first end piece formed by first ends of the first and second partially tubular members, and a second end piece formed by second ends of the first and second partially tubular members. The method may also include delivering electrical energy to the body lumen via at least one of the first or second plurality of legs.

In a further example, the legs of first partially tubular member circumferentially may alternate with legs of the second partially tubular member.

In yet another aspect, the present disclosure may be directed to a medical device. The medical device may include an expandable energy delivery array reciprocally movable between a first configuration and a second configuration. The expandable energy delivery array may include a first assembly having a first proximal end piece, a first distal end piece, and one or more first energy transfer elements extending between the first proximal and first distal end pieces, and a second assembly having a second proximal end piece, a second distal end piece, and one or more second energy transfer elements extending between the second proximal and second distal end pieces. The second proximal end piece may be proximal to the first proximal end piece, and the second distal end piece may be distal to the first distal end piece.

Various examples of the present disclosure may include one or more of the following features: wherein the first and second assemblies may be electrically insulated from one another; wherein the first and second proximal end pieces may be separated by an insulating element; wherein the first and second proximal end pieces may be longitudinally separated by the insulating element; wherein the first and second distal end pieces may be longitudinally separated by an insulating element; wherein the first and second energy transfer elements may radially alternate with one another relative to a longitudinal axis of the medical device; wherein the second energy transfer elements may extend through a notch disposed in an outer radial surface of the second distal end piece; wherein the first energy transfer elements may be disposed further from a longitudinal axis of the energy delivery array than the second energy transfer elements; wherein the second assembly may be configured to deliver energy through a body tissue to the first assembly; further including an activation element that may extend from a proximal end of the medical device through the first and second assemblies, the activation element being coupled to the second distal end piece; wherein longitudinal movement of the activation element may be configured to reciprocally move the energy delivery array between the first and second configurations, wherein the first configuration is a collapsed configuration and the second configuration may be a radially expanded configuration; wherein the activation element may be configured to deliver RF energy to the second assembly; wherein each of the first and second transfer elements may include an active region defined at proximal and distal portions by insulating regions, wherein the active region may be configured to deliver RF energy to body tissues when in contact with the body tissues, and the insulating regions are not configured to deliver RF energy to body tissues at any time; wherein the active region of at least one first or second energy transfer element may include at least one temperature sensing element configured to sense a temperature of the active region or of body tissue; wherein the energy delivery array may be configured to deliver energy to body tissues in a bipolar configuration.

In yet another aspect the present disclosure may be directed to a medical device. The medical device may be an expandable energy delivery array reciprocally movable between a first configuration and a second configuration. The expandable energy delivery array may include one or more first energy transfer elements, and one or more second energy transfer elements. The one or more first energy transfer elements may alternate with the one or more second energy transfer elements radially about a longitudinal axis of the energy delivery array, and the one or more first energy transfer elements may be spaced further from the longitudinal axis of the energy delivery array than the one or more second energy transfer elements.

Various aspects of the present disclosure may also include the following feature: an activation element that may extend from a proximal end towards a distal end of the medical device, the activation element configured to deliver energy to the one or more second energy transfer elements.

In yet another aspect, the present disclosure may be directed to a method of delivering energy to a body. The method may include inserting an energy delivery array having one or more first energy transfer elements and one or more second energy transfer elements into a lumen of the body. The one or more first energy transfer elements may be disposed further from a longitudinal axis of the energy delivery array than the one or more second energy transfer elements. The method may also include radially expanding the one or more first and second transfer elements to contact tissues defining the lumen, and delivering energy from the one or more second energy transfer elements, through the tissues, to the one or more first energy transfer elements.

Various aspects of the present disclosure may include one or more of the following features: radially expanding the one or more first and second transfer elements by longitudinally moving an activation element extending through a space defined by the first and second energy transfer elements; and delivering energy to the one or more second energy transfer elements via the activation element.

BRIEF DESCRIPTION OF THE DRAWINGS

The accompanying drawings, which are incorporated in and constitute a part of this specification, illustrate exemplary examples of the present disclosure and together with the description, serve to explain principles of the disclosure.

DESCRIPTION OF THE EXAMPLES

Reference will now be made in detail to exemplary examples of the present disclosure, examples of which are illustrated in the accompanying drawings. Wherever possible, the same reference numbers will be used throughout the drawings to refer to the same or like parts. The term "distal" may refer to the end farthest away from a user when introducing a device into a patient. By contrast, the term "proximal" may refer to the end closest to the user when placing the device into the patient.

Examples of the present disclosure relate to medical devices used for applying energy to tissue during minimally invasive procedures. For example, examples of a disclosed catheter and method of use are contemplated. In some examples, an expandable catheter, e.g., a radiofrequency (RF) catheter, including elongated electrodes (configured in an expandable electrode array) may be advanced into tissue of a patient's body. The catheter may be bipolar or monopolar, and may be configured to expand within a body lumen to deliver electrical energy to elongated electrodes located at a distal portion of the catheter. The catheters may be constructed without welding the electrodes together. In particular, the catheter can be used in a procedure, such as, e.g., an energy delivery procedure, where energy may be transferred to target tissue (e.g., lung tissue) by the RF catheter electrode. Energy delivery procedures may use the catheter to deliver thermal energy to an airway wall in a controlled manner to eliminate or otherwise reduce excessive ASM. To apply an energy during an energy delivery procedure, the catheter may be positioned at a desired location within the airway. An electrode cage or array may be disposed at a distal portion of the catheter, and may be selectively expanded to contact the airway wall. The RF electrodes may be expanded manually by squeezing a handle (or actuating another suitable actuator) of the catheter by applying an appropriate expansion force.

Initially, those of ordinary skill in the art will understand that any of the examples disclosed herein may include one or more of the features discussed in connection with another of the other examples disclosed herein.

Figure 1:
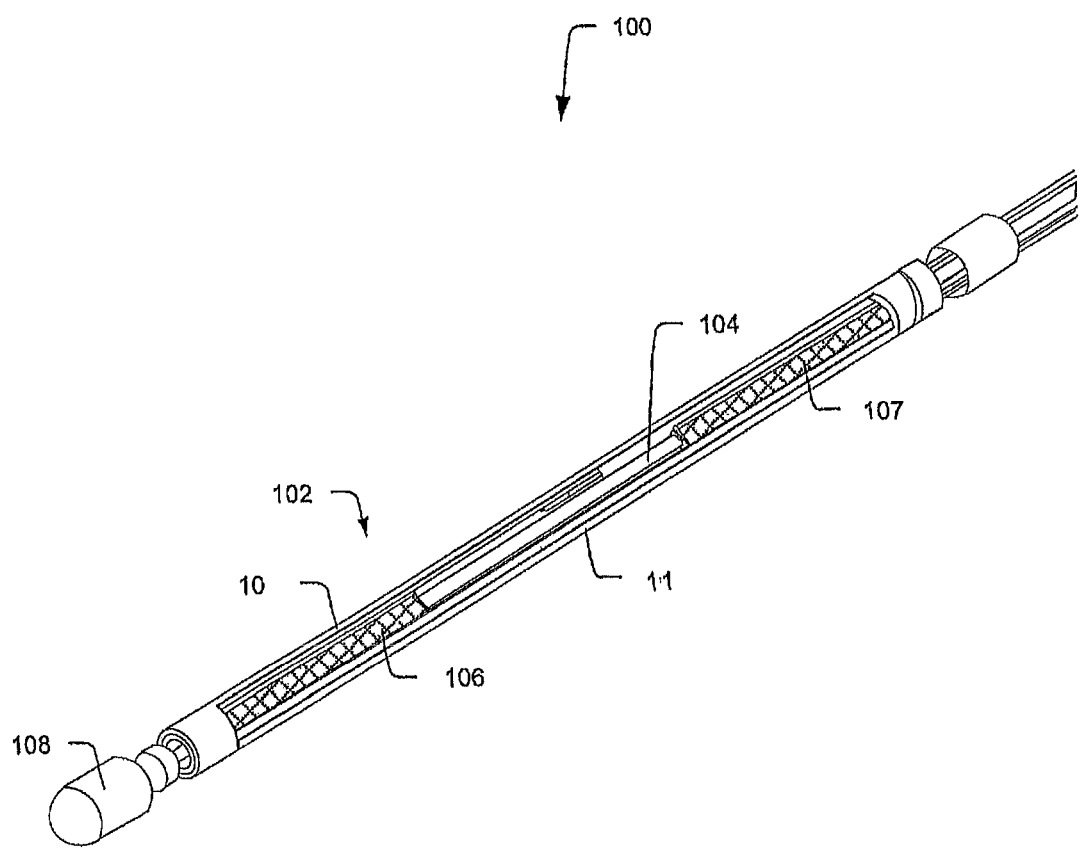
FIG. 1 is a perspective view of a distal electrode array of an exemplary catheter in a collapsed configuration, according to an example of the present disclosure.
Figure 5:
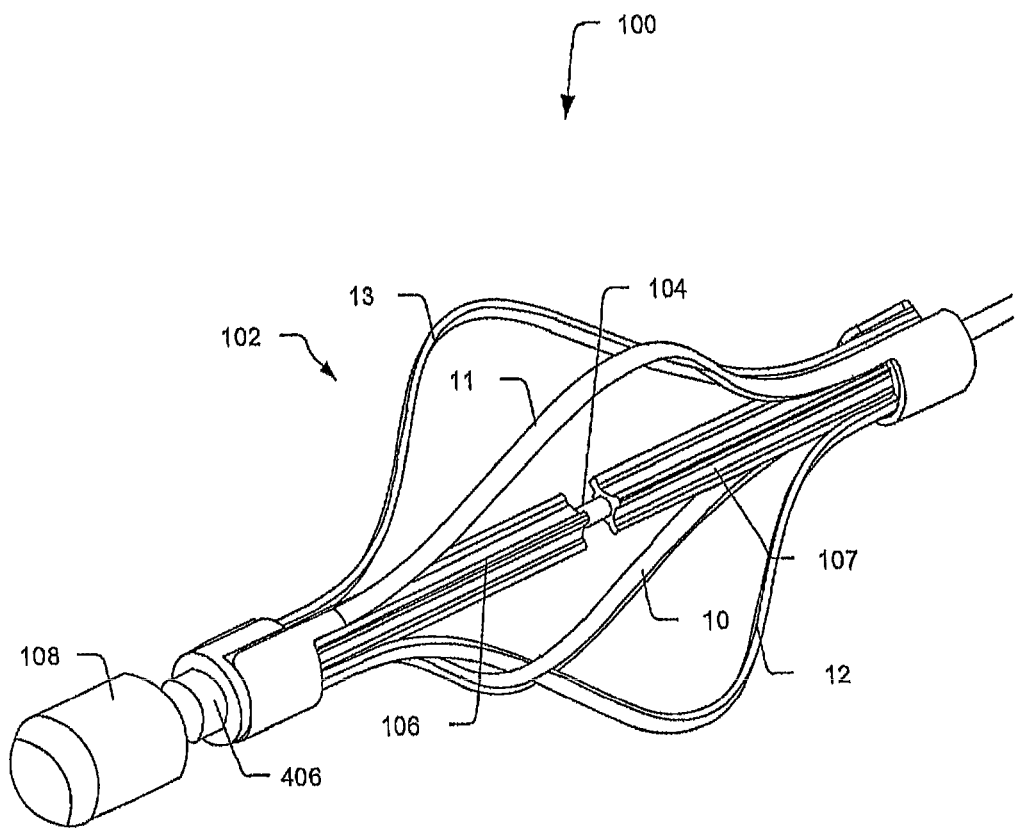
FIG. 5 is a perspective view of the distal electrode array of FIG. 1 in an expanded configuration.

FIG. 1 is a perspective view of a distal portion of an exemplary catheter 100 having an electrode array or cage 102 in a collapsed configuration. Catheter 100 may be configured to be introduced into a patient's body through an incision or a suitable natural opening, such as e.g., the mouth or nose. In one exemplary example, catheter 100 may be configured to be advanced to a desired location within a patient's body via a suitable introduction sheath (not shown), such as, e.g., an endoscope, bronchoscope, or other type of scope. The proximal end of the catheter may be connected to a hub assembly, a handle (not shown), or another suitable actuator for operating cage 102. More particularly, the handle or actuator may be configured to transition cage 102 between a first collapsed configuration (e.g., as shown in FIG. 1) and a second expanded configuration (e.g., as shown in FIG. 5). The handle may be ergonomically designed and may include a variety of components such as, e.g., steering controls and a pull wire for selectively positioning a distal portion of catheter 100. Further, the handle may include one or more ports in communication with one or more working channels of the introduction sheath for inserting other medical device(s).

The distal portion of catheter 100 may be used to ablate or otherwise deliver energy to tissue inside the body of a patient for treatment. As shown in FIG. 1, the distal portion of catheter 100 may include electrode cage 102, an activation element 104 (such as, e.g., a pull wire), expansion supporters 106 and 107, and a hypotube or cap 108. Electrode cage 102 may be formed from two separate electrode tubes operably received into one another, as discussed below in greater detail. The electrode tubes may include one or more electrode ribbons 10 and 11, each of which may be separated from one another by a longitudinal gap 18, and may be configured into monopolar or bipolar configurations for delivering energy tissue. as described below. The distal and proximal ends of the electrode tubes may have an opening for allowing activation element 104 to extend distally from the proximal portion of catheter 100 through electrode cage 102. Unlike conventional electrode cages or electrode arrays, electrode cage 102 may be constructed without welding electrodes 10, 11 together on catheter 100, and may be operated in a bipolar configuration by isolating positive electrodes from negative electrodes.

A length of activation element 104 extending through electrode cage 102 may also extend through expansion supporters 106, 107. Expansion supporters 106, 107, the longitudinal gaps between the electrodes 10, 11, and a hypotube 108 may facilitate buckling of electrodes 10, 11. The buckling of electrodes 10, 11 may allow electrode cage 102 to reciprocally move between the collapsed configuration and an expanded configuration, in which each electrode of the electrode cage bows radially outward. In some examples, electrodes 10, 11 may include a shape memory material that restores electrodes 10, 11 to the collapsed or expanded configuration. Hypotube or cap 108 may be located at a distal end of the electrode cage 102 to support and provide resilience to electrode cage 102.

FIGS. 2A-2H, 3A-3E, and 4A-4B illustrate various views of the components and assemblies that make up electrode cage 102 depicted in FIG. 1. The subsequent disclosure describes an exemplary example of forming electrode cage 102 from electrode panels 202 and 203, (referring to FIGS. 2A-2H). Electrode cage 102 may include a channel 302 (referring to FIGS. 3A-3C) for a thermocouple (TC) element 304 (e.g., wire), and a shrink tube 306 (referring to FIGS. 3D-3E) configured to provide strain relief to electrode cage 102. Electrode panels 202, 203 can be coupled to an end cap 402 (FIG. 4A), activation element 104 (FIG. 4B), expansion supporters 106, 107 and hypotube 108 (FIG. 5) to manufacture the distal portion of catheter 100.

In one example, each of electrode panels 202, 203 (referring to FIG. 2A) may be formed from a single sheet of any biocompatible material that is both flexible and electrically conductive in nature. The sheet may be rectangular or may be another suitable shape. The biocompatible material may include, but is not limited to, stainless steel, nitinol, other known electrically conductive surgical/medical materials, and any combinations thereof. During manufacture, electrode panel 202 may be formed from a sheet having a distal portion 22 and a proximal portion 24 that can be machined or etched to achieve a variable thickness cross-section. Similarly, electrode panel 203 may be for formed from a sheet having a distal portion 23 and a proximal portion 25. The distal portions 22, 23 and proximal portions 23, 25 of the various sheets may be also machined such that they are wider relative to a remainder of the sheet(s).

Longitudinal sections may be removed from between distal portion 22 and proximal portion 24 of electrode panel 202 to form electrodes 10 and 11 separated by a longitudinal gap 18. Similarly, the electrode panel 203 may have electrode ribbons 12 and 13 separated by a longitudinal gap 20. Although each of the electrode panels 202, 203 have been shown to have two electrodes, a greater or lesser number of electrodes may be utilized in alternative examples. The removal of the longitudinal sections may cause the transverse lengths of distal portion 22 and proximal portion 24 of electrode panel 202 to become relatively longer than the combined width of electrodes 10, 11 and longitudinal gap 18. Similarly, the removal of the longitudinal sections may cause the transverse lengths of distal portion 23 and proximal portion 25 of electrode panel 203 to become relatively longer than the combined width of electrodes 12, 13 and longitudinal gap 20, The electrodes 10, 11, 12, and 13 may be longitudinally extending legs having substantially the same or a variable cross-section, each of which may be less than the width of inclusive longitudinal gaps 18, 20. As shown, electrodes 12, 13 may have a thicker cross-section at an interior portion (e.g., at a middle or central portion) for providing additional strength to electrodes 12, 13 and space for creating a channel. The sheets utilized to form electrode panels 202, 203 may have relatively different widths so that the electrode panels 202, 203 have different diameters when rolled.

Subsequently, electrode panels 202, 203 may be rolled to form a partially tubular member (FIG. 2B) such that each of electrode panels 202, 203 has a radial profile. When rolled, electrode panels 202, 203 may form electrode tubes 204, 205 respectively. The radial profile may create a C-shaped cam surface at the longitudinal ends of the electrode tubes 204, 205, allowing electrode tube 204 to surround and mate with electrode tube 205, forming electrode cage 102. For instance, radially distal portion 22 and proximal portion 24 of the electrode tube 204 may operably receive the respective radially distal and proximal portions 23, 25 of electrode tube 205 using any suitable mechanism (FIG. 2C), such as, e.g., welding, coaxial sliding, friction fitting, screw fitting, and gluing, among others. Unlike in conventional catheters, where formation of an electrode cage or array may be achieved by welding the electrodes as a bundle, electrode tubes 204, 205 may be instead received into one another (e.g., one may be inserted into a volume partially defined by the other). Consistent with this, electrode cage 102 may have a C-shaped opening at its distal and proximal portions. The outer diameter and inner diameter of electrode tubes 204, 205 may determine the effective force responsible for interlocking electrode tubes 204, 205 to form electrode cage 102. Such interlocking of the electrode tubes 204, 205 may allow for expansion of electrode cage 102 about the distal portions 22, 23 and the proximal portions 24, 25 of electrode tubes 204, 205. Additionally, the interlocking of the C-shaped radial ends may prevent rotation of the electrodes 10, 11, 12, and 13 relative to each other. Electrode tubes 204, 205 may be retained relative to one another via an interference or friction fit.

Figure 2A:
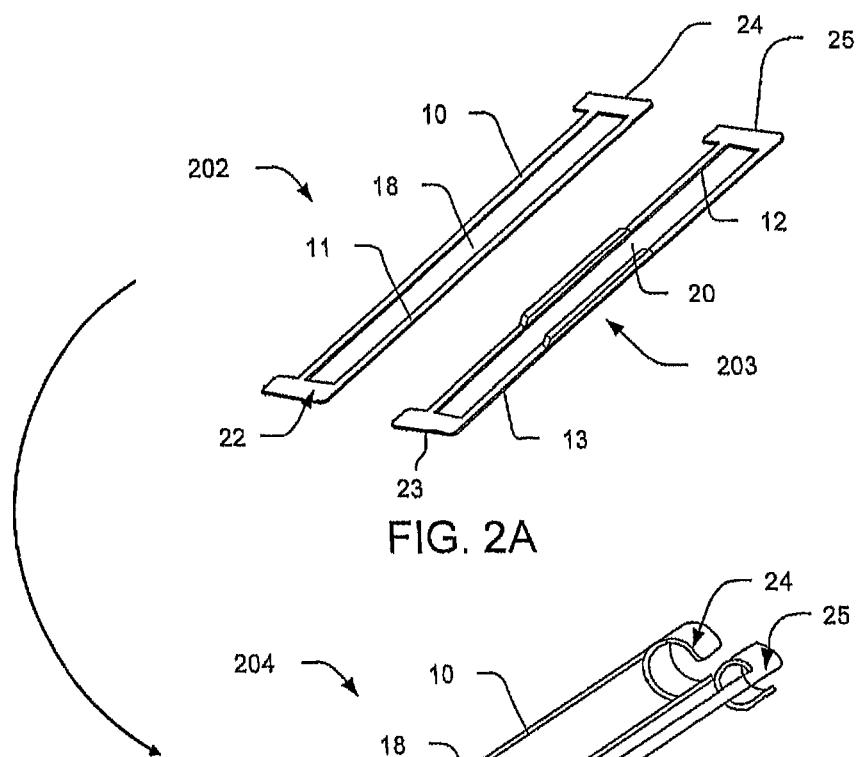
FIGS. 2A-2H illustrate exploded, partially exploded, and assembled views of an exemplary electrode array.
Figure 2B:
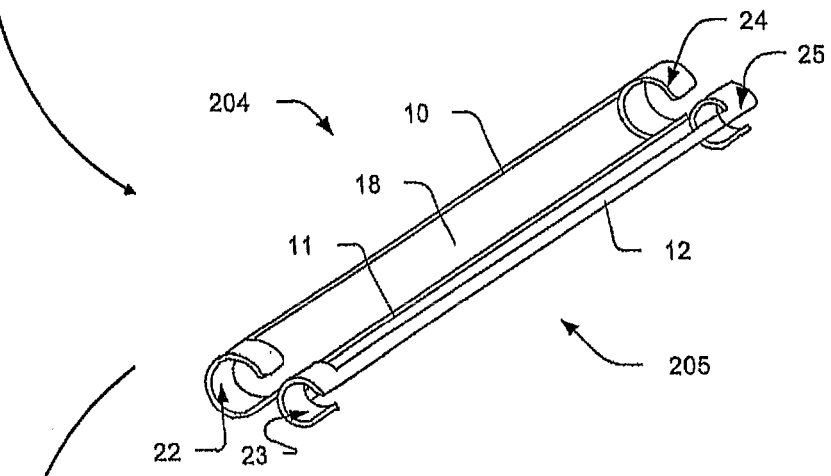
Figure 2C:
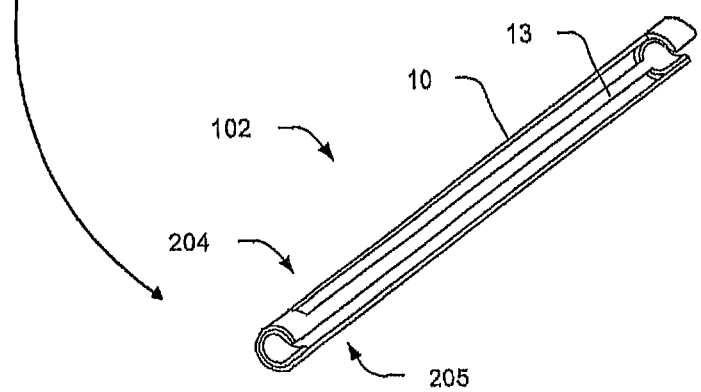
Figure 2D:
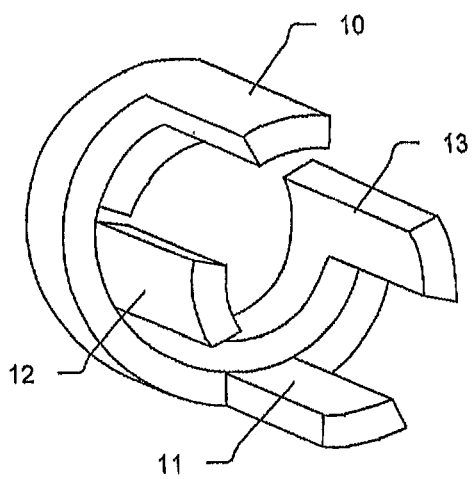
Figure 2E:
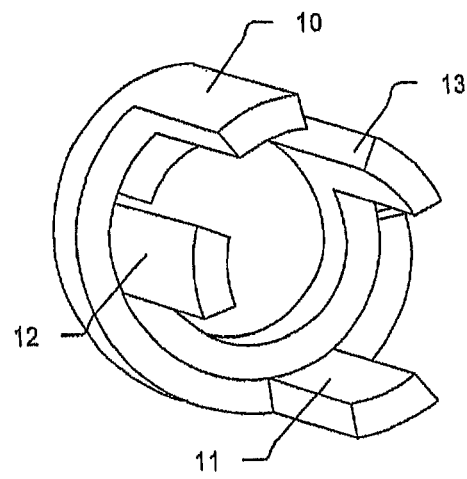

Further, the angular position of the electrodes 10, 11,12, and 13 in electrode tubes 204, 205 can be controlled by the orientation of longitudinal gaps 18, 20 between them. That is, electrode tubes 204, 205 may be rotated relative to one another (as shown in FIGS. 2D and 2E) to, e.g., control the spacing between electrodes 10, 11, 12, and 13. Coplanarity of the distal and proximal edges of electrode tubes 204, 205 may be maintained to properly align the electrodes. Moreover, longitudinal gaps 18, 20 may allow for compression and/or buckling of electrode cage 102 during operation.

In electrode cage 102, inner electrode tube 205 may be detachably connected or permanently coupled to outer electrode tube 204 with either even spacing (FIG. 2D) or uneven spacing (FIG. 2E) between electrodes 10, 11, 12, and 13. Electrodes 10, 11, 12, and 13 may be spaced evenly along the circumference of electrode cage 102 to account for the diametric difference(s) of inner electrode tube 205 with respect to outer electrode tube 204. The circumference of the electrode cage 102 at its longitudinal ends may account for uneven spacing between the electrodes 10, 11, 12, and or 13.

Figures 2F, 2G:
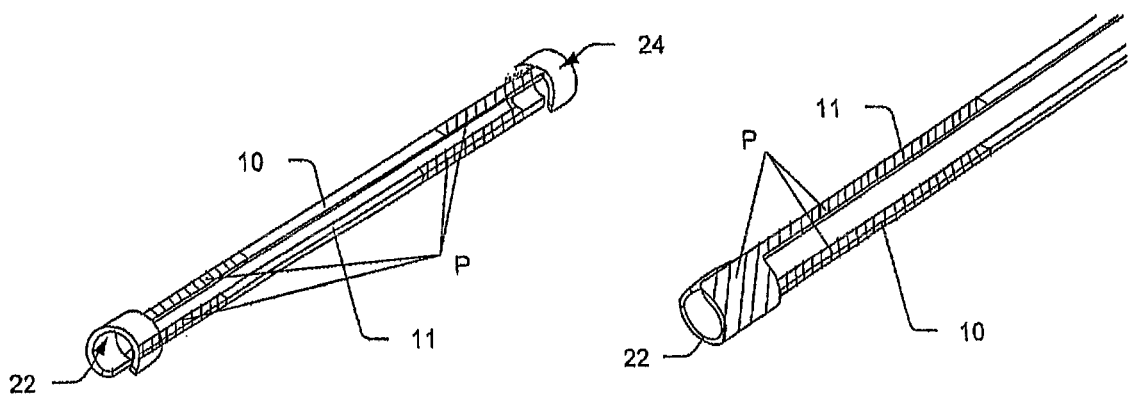
Figure 2H:
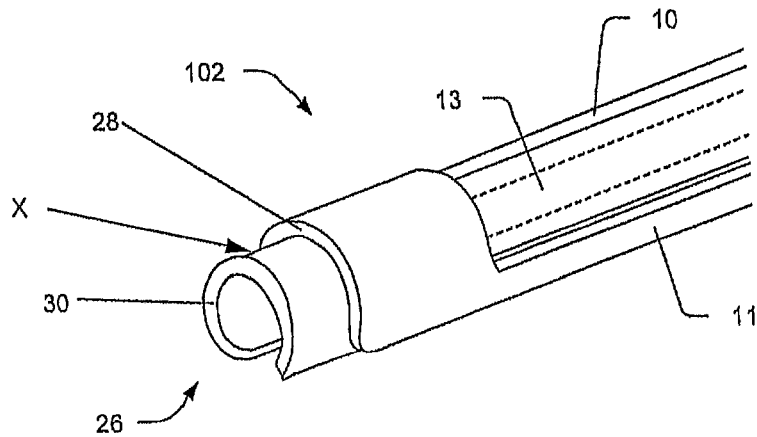

Electrode cage 102 may be monopolar or bipolar based on insulation arrangements between electrodes 202, 203. If electrodes 10, 11, 12, and 13 are not insulated from each other at one or both of distal portions 22, 23 and proximal portions 24, 25, electrode cage 102 may operate in monopolar fashion (FIG. 2F). If electrodes 10, 11, 12, and 13 are insulated from each other at distal portions 22, 23 and proximal portions 24, 25, electrode cage 102 may operate in a bipolar fashion (FIG. 2G). Moreover, as shown in FIGS. 2F and 2G, portions P of electrodes 11 (represented by a cross-hatch) may be insulated to create a focused region at an interior portion of electrodes 10, 11 for delivery of electrical energy. Similarly, portions of electrodes 12, 13 may be insulated to create a focused region for delivery of electrical energy. In order to achieve the above-described insulation characteristic, electrode tubes 204, 205 may be coated with any suitable insulative material, for example, a hydrophilic layer of polymers known in the art at contact regions disposed at distal portions 22, 23 and proximal portions 24, 25. Other suitable insulative coatings may include ceramic, silicone, glass, and any other non-conductive, biocompatible material The coating may occur prior to the assembly of electrode tubes 204, 205. The coating of electrode tubes 204, 205 may promote the localization of radiofrequency (RF) electrical energy at interior portions of electrode tubes 204, 205. The insulative material may be applied by a variety of coating process including vapor deposition, dipping, spraying, or other processes that are conducive for small parts and thin films. The insulations described above may also serve to electrically separate electrodes 10-13 so that cage 102 may operate in a bipolar configuration.

An offset X may be disposed between electrode tubes 204, 205 (FIG. 2H), and may be allotted at distal end 26 of electrode cage 102 to aid in the assembly of electrode cage 102. For example, offset X may allow inner electrode tube 205 to be compressed independently from outer electrode tube 204. Further, electrical energy may be supplied to inner electrode tube 205 by activation element 104 if, for example, in the bipolar configuration, distalmost surfaces 28, 30 (referring to FIG. 2H) of outer and inner electrode tubes 204, 205 respectively are exposed to contact a portion of activation element 104 that is conducting electrical energy. In a bipolar configuration, e.g., distalmost surface 28 may be insulated from distalmost surface 30, which may be in contact with activation element 104 and receiving electrical energy therefrom.

Figure 3A:
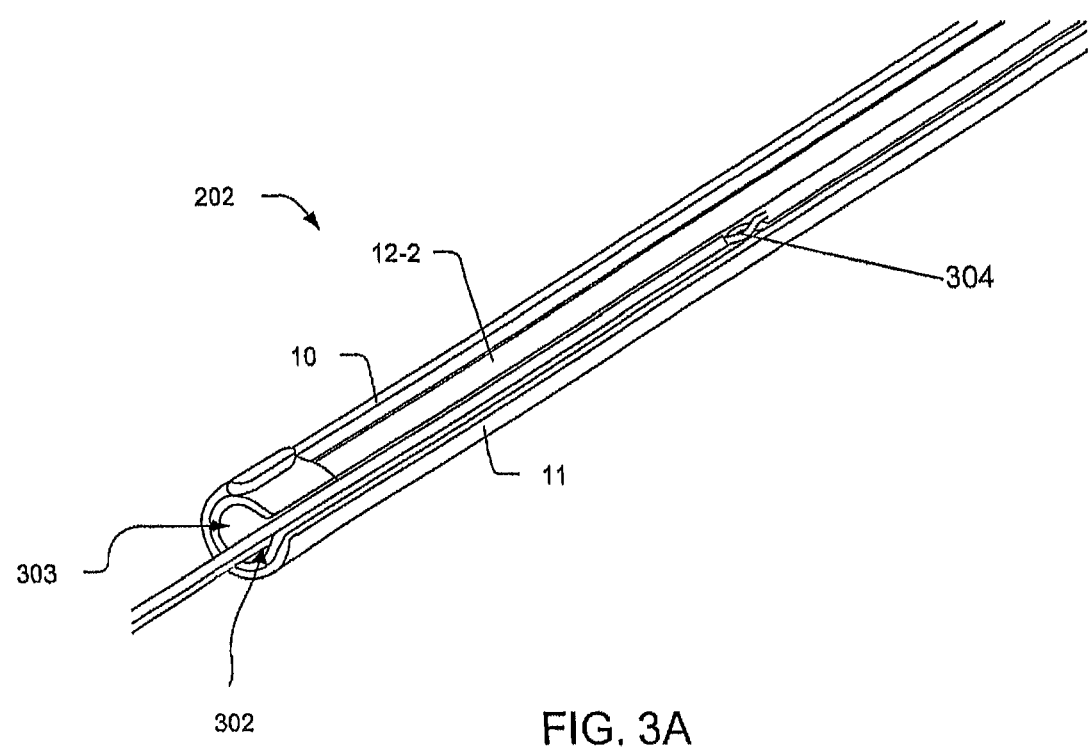
FIGS. 3A-3E depict alternative configurations of an exemplary electrode array.
Figure 3B:
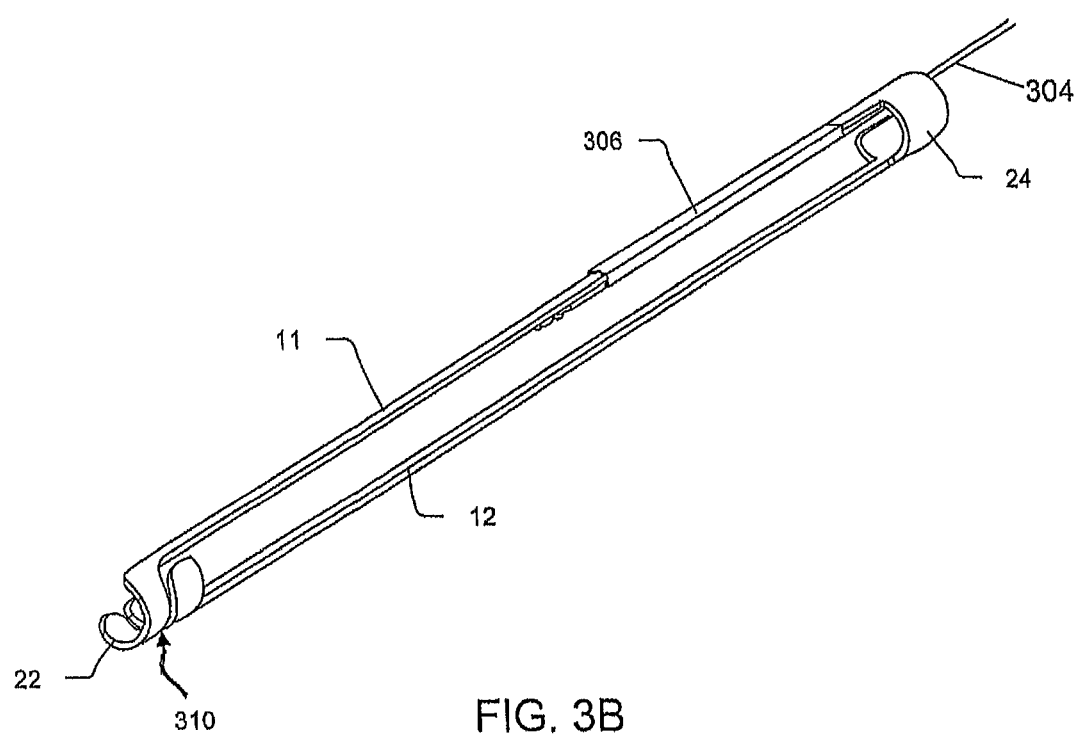
Figure 3C:
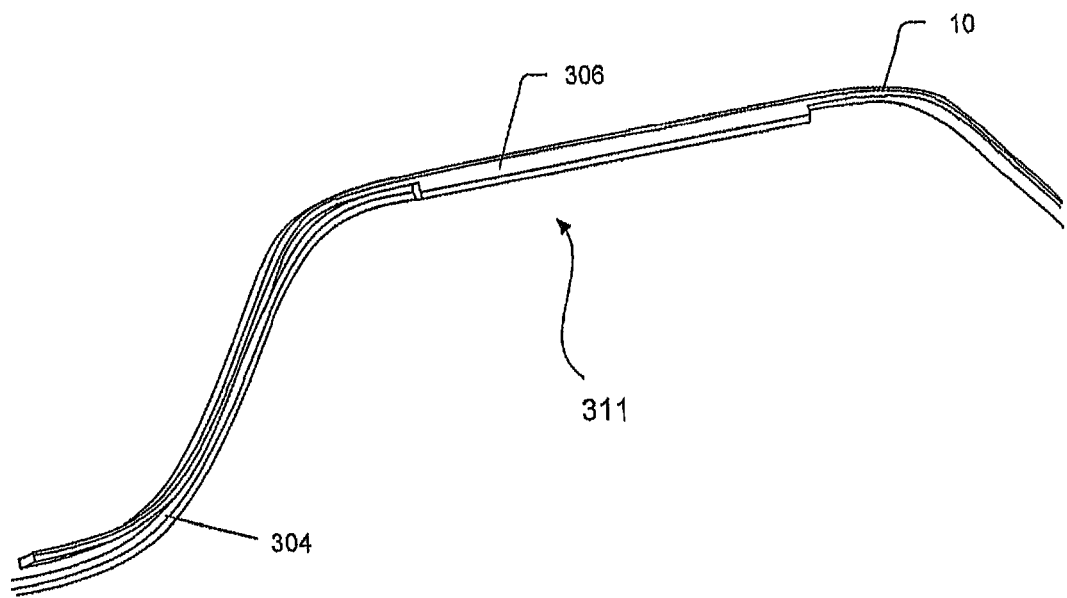
Figure 3D:
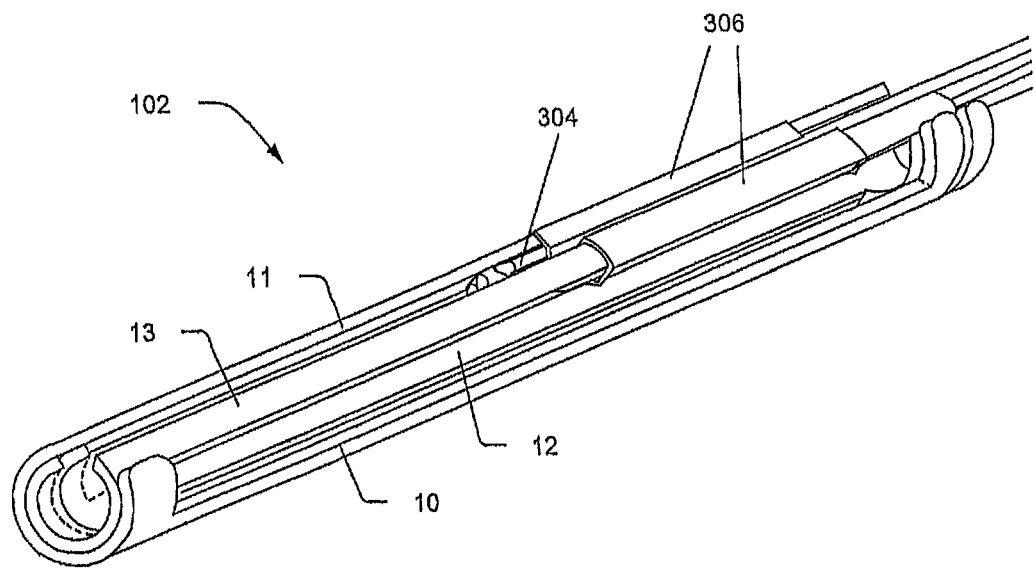
Figure 4A:
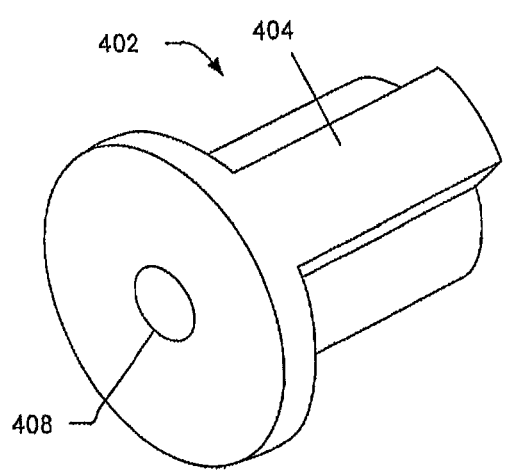
FIGS. 4A-4B depicts an exemplary cap for use with the exemplary electrode arrays disclosed herein.

Referring to FIG. 3A, proximal and/or distal ends of electrode tubes 204, 205 may be generally C-shaped. However, those of ordinary skill will recognize that the proximal and/or distal ends of tubes 204, 205 may include any suitable configuration. When electrode tubes 204, 205 are interlocked, they may define a longitudinally extending gap 302. The proximal and/or distal ends of electrode tubes 204, 205 may partially define an incomplete annular channel 303 due to the presence of gap 302. In one example, gap 302 may be formed in an external portion of electrode tubes 204, 205, and be configured provide access to channel 303 for, e.g., thermocouple (TC) element(s) (e.g., wires) 304 that extend from a proximal portion of catheter 100. TC element(s) 304 may be configured to determine a temperature of electrodes 10, 11, 12, and 13 (or surrounding tissue which the electrodes may contact) during operation. In another example, elements (e.g., wires) for supplying electrical energy to electrodes 10, 11, 12, and 13 may be routed through channel 303 via gap 302 from the proximal portion of catheter 100. As shown in FIG. 3A, electrode cage 102 may expand about its radial ends, and thus access to electrodes 10, 11, 12, and 13 through electrode cage 102 for soldering or welding of TC element 304 may be relatively easy compared to other configurations. The TC element 304 may follow insulation coating on electrodes 10, 11, 12, and 13, and may be disposed on electrodes 10, 11, 12, and 13 prior to the assembly of electrode tubes 204, 205. Further, TC elements 304 may be secured within channel 303 through an additional compression applied on respective electrode tubes 204, 205, or by positioning TC element(s) 304 into channel 303 and subsequently attaching TC element(s) 304 to an interior surface of channel 303 by bonding, welding, or soldering, or by another suitable securing mechanism.

Figure 3E:
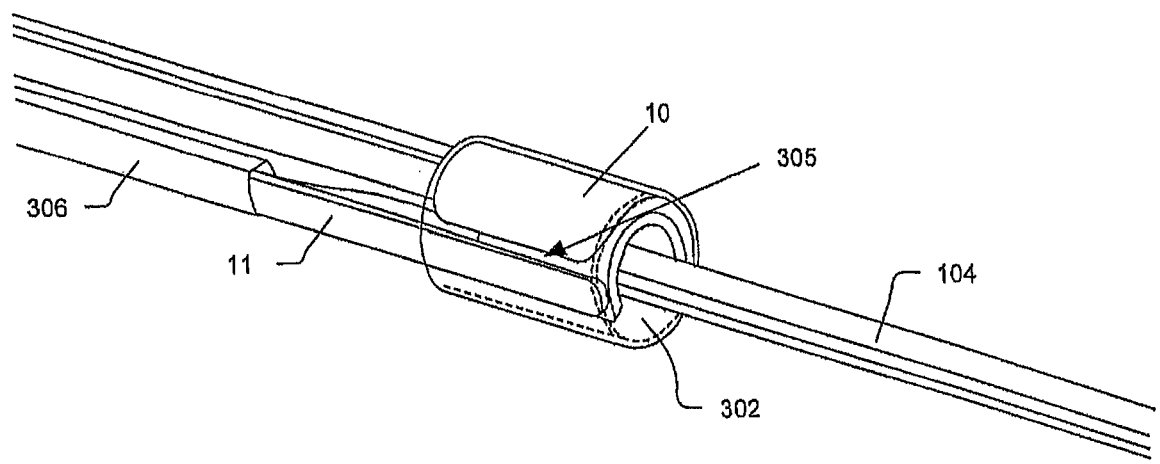

Referring to FIG. 3E, the C-shaped ends of electrode tubes 204, 205 may further define a longitudinally extending gap 305 to accommodate a shrink tube 306. Gap 305 may be substantially parallel to gap 302, and may be transposed about a circumference of the C-shaped ends of electrode tubes 204, 205 with respect to gap 302. Shrink tube 306 may be configured to provide strain relief for the electrode-attached elements such as TC element 304 and electrodes 10, 11, 12, and 13. In one example (referring to FIG. 3B-3E), gap 305 may receive TC element 304 and shrink tube 306. In an alternative example (referring to FIGS. 3B-3E), electrode tubes 204, 205 may be oriented in electrode cage 102 to create a single channel 302 at one end of electrode cage 102 for receiving TC element 304 and shrink tube 306. Channel 302 may decouple one end of the electrode, for example, the electrode 10, from a remainder of electrode tube 204. The C-shaped ends of electrode tubes 204, 205 may define a circumferentially extending gap 310 that decouples electrodes 11 and 12 at one end (e.g., the proximal or distal end) of electrode tubes 204, 205. In another example (referring to FIG. 3C), a channel 311 may be created between electrode 10 and shrink tube 306 disposed over a thicker cross-section of electrode 10. In this example, channel 311 may receive TC element 304 along a thicker cross-section of electrode 10 and a C-shaped proximal or distal end of electrode cage 102. Shrink tube 306 may be slid through channel 311 as well as over TC element 304 (referring to FIG. 3D). Shrink tube 306 may be subsequently heated to permanently affix shrink tube 306 over TC element 304 to provide strain relief. Channel 311 may provide additional stiffness to the electrodes, and may produce improved tissue airway contact when electrode cage 102 is expanded. Referring to FIG. 3E, the outer electrode tube 204 may fix channel 302 adjacent to the distal end of electrode cage 102. However, channel 302, which may be disposed in the outermost electrode electrodes 10, 11 at the proximal end of electrode cage 102, may be gripped by shrink tube 306.

Further, once electrode tubes 204, 205 are interlocked to form electrode cage 102, an end cap 402 may be inserted into the distal end of electrode cage 102 (referring to FIG. 4A) to maintain the inner diameter and orientation of electrode cage 102. In some examples, cap 402 may urge inner electrode tube 204 radially outward and against outer electrode tube 205, thereby creating a friction fit therebetween. A coaxial hole 408 disposed in end cap 402 may be created to allow activation element 104 to distally pass through it. End cap 402 may also include a rib 404 to engage with channel 302 created by electrode tubes 204, 205 at the C-shaped distal end of electrode cage 102. Rib 404 in end cap 402 may maintain orientation of electrode tubes 204, 205 with respect to one another. Rib 404 may also urge opposing ends of inner electrode tube 204 away from one another, thereby enlarging a diameter of inner electrode tube 204 and consequently urging it against outer electrode tube 205. End cap 402 may be modified or configured to include insulation and to accommodate the offset X (see FIG. 2H) between electrode tubes 204, 205. In a bipolar configuration having C-shaped contact regions of the electrodes 10, 11, 12, and 13 insulated from each other at the distal end of electrode cage 102, modified end cap 402 may be configured to conduct electrical energy from activation element 104 to only one of the electrode tubes, for example, the electrode tube 205. Thus, in some examples, modified end cap 402 may be placed in communication with conducting distal ends of the C-shaped contact regions of any combination of electrodes 10, 11, 12, and 13.

Figure 4B:
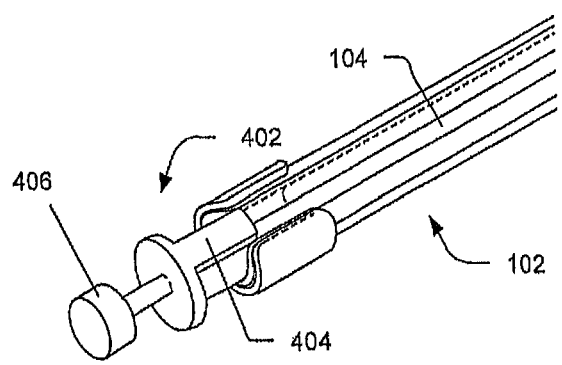

Referring to FIG. 4B, activation element 104 may extend distally from within electrode cage 102 through channel 302 in at least one example. A distal end of activation element 104 can include a stopper 406 that distally engages and passes through coaxial hole 408 in end cap 402. Stopper 406 may include a diameter that is larger than a remainder of activation element 104. End cap 402 may be inserted in communication with the distal end of electrode cage 102. Stopper 406 may help provide stability, grip and assist in reciprocal movement of electrode cage 102 from a collapsed configuration to an expanded configuration during operation.

FIG. 5 illustrates electrode cage 102 in the expanded configuration. Configurations of electrode cage 102 based on orientation of electrode tubes 204, 205 and spacing between electrodes 10, 11, 12, and 13 and activation element 104 may be provided with expansion supporter(s) 106, 107 to assist in an electrode buckling direction and to prevent electrode inversion. Expansion supporters 106, 107 may also function as alignment components to maintain spacing between electrodes 10, 11, 12, and 13 when they are in the expanded configuration. Each of expansion supporters 106, 107 may include a longitudinal lumen disposed therein for receiving a portion of activation element 104.

A system may include a controller (not shown) and a standard flexible bronchoscope including catheter 100. The controller may be configured to deliver RF electrical energy to electrodes 10, 11, 12, and 13 at the distal portion of catheter 100. During operation, catheter 100 may be, while in collapsed configuration, distally advanced into a body lumen, such as, e.g., a bronchial tree or airway of lungs through a natural opening of the body, such as, e.g., the nose or mouth. The bronchoscope may be then navigated to a target treatment site, for example, the most distal airway in a targeted bronchial lobe. Once a distal end portion of catheter 100 is positioned at the target treatment site, electrode cage 102 may be expanded to make electrodes 10, 11, 12, and 13 contact an inner wall of the airway. Expansion of electrodes 10-13 may be limited when contact is made with the inner airway wall. Subsequently, the controller, which may be connected to a hub assembly of catheter 100 at the proximal end, may be activated to deliver electrical energy via activation element 104 and electrodes 10, 11, 12, and 13 to the treatment site. The electrical energy may be delivered in monopolar or bipolar fashion by electrodes 10, 11, 12, and 13 to deliver energy (e.g., RF, ultrasonic, or thermal energy) to tissue, such as, e.g., lung tissue. Each of such activation of electrodes 10, 11, 12, and 13 may be controlled to deliver RF electrical energy at a certain power, temperature and/or period of time, in order to affect a certain treatment protocol, e.g., 10 seconds intervals, at a temperature of about 65 degrees Celsius, and up to about 15 Watts of power, in the case of a monopolar application. It should be noted that the activation period may be increased or decreased, if desired. However, the bipolar activation of electrodes 10, 11, 12, and 13 may reduce this activation period relative to the monopolar activation period. The delivered electrical energy may be controlled to create a precise delivery of thermal energy to the airway wall, e.g., to eliminate or otherwise reduce excessive ASM, and decrease the ability of the airways to constrict, thereby reducing the severity of COPD or other bronchial conditions. In some examples, this may reduce the frequency of asthma attacks. When the lung tissue or ASM is sufficiently reduced, or treatment is otherwise completed, e.g., the controller may be deactivated and activation element 104 may be relaxed to release the buckling of electrodes 10, 11, 12, and 13 to return electrode cage 102 to the collapsed configuration, so that catheter 100 may be removed from within the patient.

This energy delivery procedure may be minimally invasive and may be performed in one or more outpatient procedure visits, each treating a different area of the lungs and scheduled approximately one or more (e.g., three) weeks apart.

Although the examples described above are disclosed in the context of use with a bronchoscope, those skilled in the art will understand that the principles disclosed above can be applied to other types of devices and can be implemented in different ways without departing from the scope of the invention as defined by the claims. In particular, constructional details, including manufacturing techniques and materials, are well within the understanding of those of ordinary skill in the art and have not been disclosed in detail herein. These and other modifications and variations are well within the scope of the present disclosure and can be envisioned and implemented by those of ordinary skill in the art.

With reference now to FIGS. 6A-6D, there is depicted another distal energy delivery assembly 700, in accordance with a further example of the present disclosure. Energy delivery assembly 700 may include one or more features of the aforementioned examples discussed herein, including, for example, electrode cage 102.

Figure 6A:
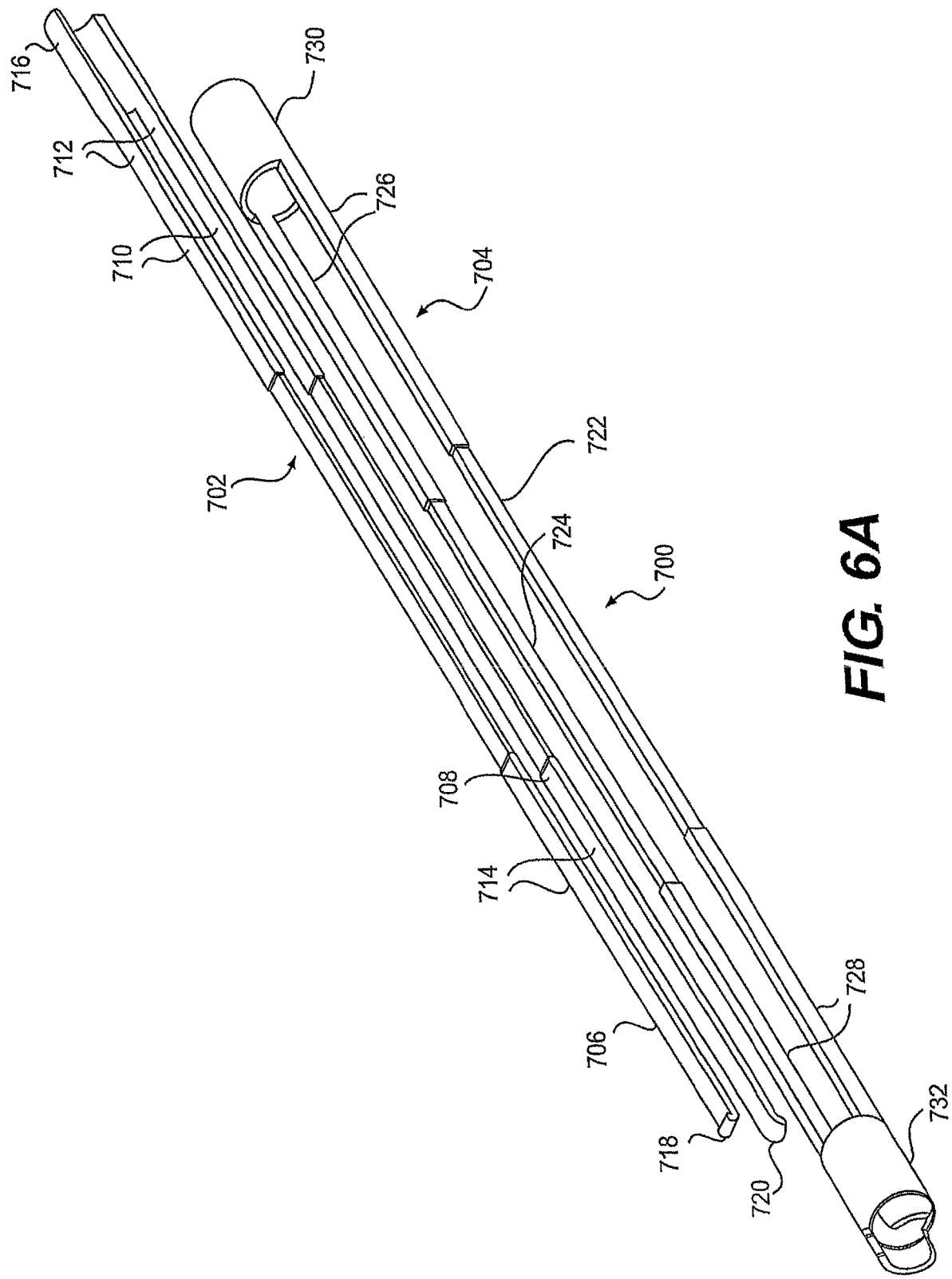
FIGS. 6A-6D illustrate exploded, partially exploded, and assembled views of another exemplary electrode array.

Energy delivery assembly 700 may include a plurality of electrode tubes 702, 704. Like electrode tubes 204, 205, electrode tubes 702, 704 may be fabricated from rolling flattened electrode panels (not shown). Electrode tube 704 may be substantially similar to one or both of electrode tubes 204, 205. For example, electrode tube 704 may include a plurality of electrodes 722, 724 separated by a longitudinal gap therebetween. Although only two electrodes 722, 724 are shown, a greater or lesser number of electrodes 722, 724 may be provided as desired. Electrodes 722, 724 may be coupled together by proximal and distal portions 730, 732, as described above in connection with the aforementioned examples. As a result of rolling, each of proximal and distal portion 730, 732 may include a C-shaped or substantially cylindrical configuration. Proximal and distal portions 730, 732 may each define a through passageway therein. One or both of electrodes 722, 724 may include insulation 726 (e.g., a suitable insulative covering) disposed on a portion of electrodes 722, 724. For example, as shown in FIG. 6A, electrodes 722, 724 may include insulation 726 disposed on a proximal portion, including proximal portion 730 of electrode tube 704. Similarly, electrodes 722, 724 may include insulation 728 disposed on a distal portion, including distal portion 732 of electrode tube 704. As discussed above, in some examples, proximal and distal portions 730, 732 may not include insulation. Electrodes 722, 724 may include an active region that does not include any insulation and disposed between insulations 726, 728. The active region may be configured to contact and deliver energy to target tissue.

Electrode tube 702 may also include two electrodes 706, 708 separated by a longitudinal gap. However, any suitable number of electrodes may be provided. Electrodes 706, 708 may be substantially similar to electrodes 722, 724. For example, electrodes 706, 708 may be coupled to one another via a proximal portion 716 having a C-shaped or substantially cylindrical configuration. Further, electrodes 706, 708 may include proximal insulation 712 (which may or may not extend to proximal portion 716) and distal insulation 714. Unlike electrode tube 704, however, distal ends of electrodes 706, 708 may be left free or otherwise unconnected to one another. That is, electrode tube 702 may not include a distal portion to couple together the distal ends of electrodes 706, 708. Instead, the distal ends of electrodes 706, 708 may include geometric features configured to secure electrode tube 702 to electrode tube 704. For example, in one example, electrodes 706, 708 may include opposing bends 718, 720, respectively, for frictionally engaging distal portion 732 of electrode tube 704. Bends 718, 720 may be preformed, or may be formed during assembly of electrode tube 702 into electrode tube 704, as described below. In such examples, a distal endface of distal portion 732 may include corresponding notches for receiving and retaining bends 718, 720 therein, as shown in FIG. 6D. Further, electrodes 706, 708 may include a substantially constant cross-sectional configuration along an entire length thereof. Alternatively, the cross-sectional configuration of one or both of electrodes 706, 708 may vary along a length thereof. For example, a proximal portion of electrode 706 may include a substantially circular cross-sectional configuration and a distal portion of electrode 706 may include a substantially rectangular or planar cross-sectional configuration.

Figure 6B:
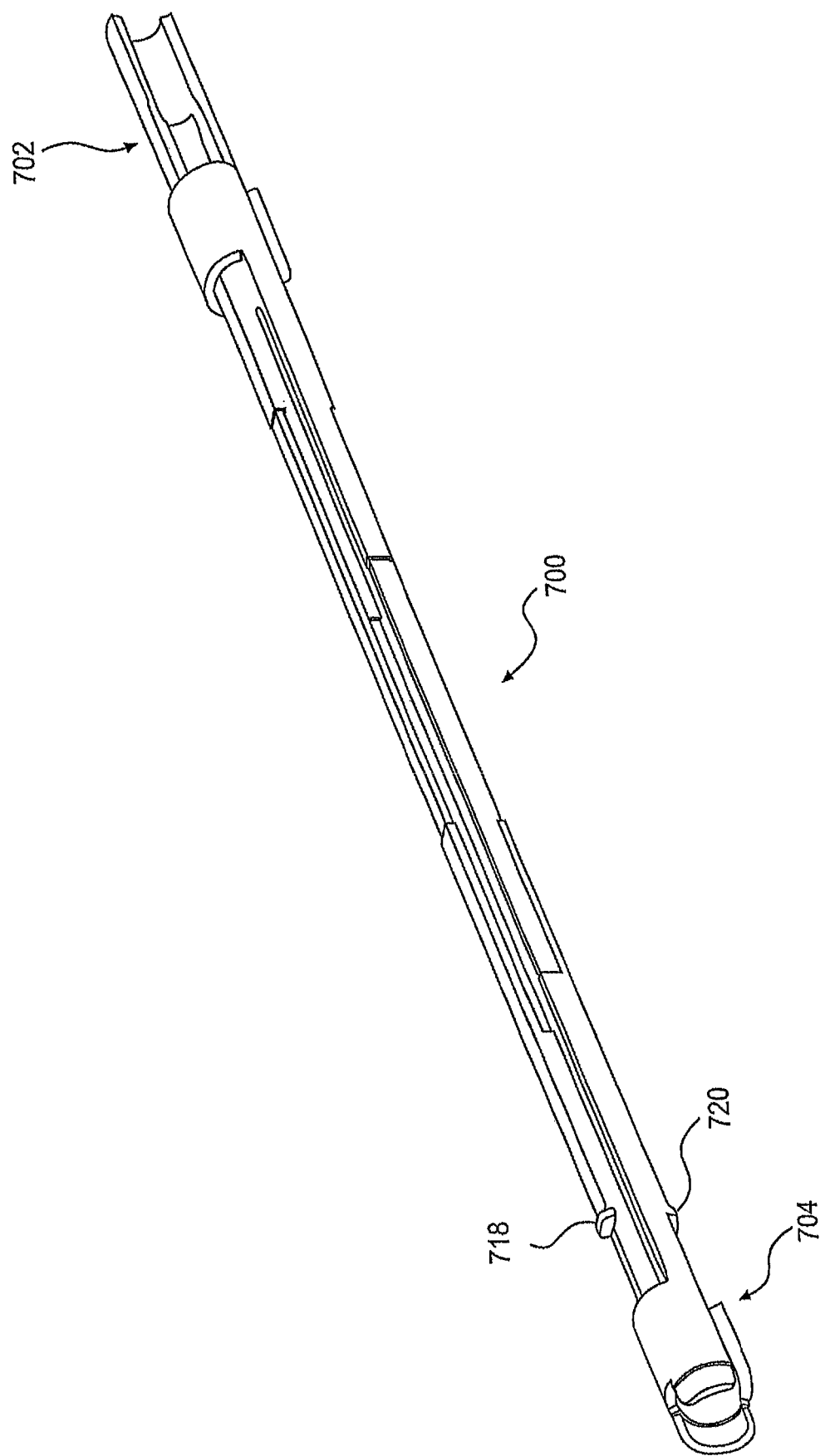

As shown in FIG. 6B, electrode tube 702 may be configured to be received within electrode tube 704. Accordingly, in some examples, electrode tube 702 may be configured to be biased radially outwardly, so that electrode tube 702 may be frictionally retained within electrode tube 702. As such, electrode tube 702, and electrodes 706, 708 may include resilient properties.

Figure 6C:
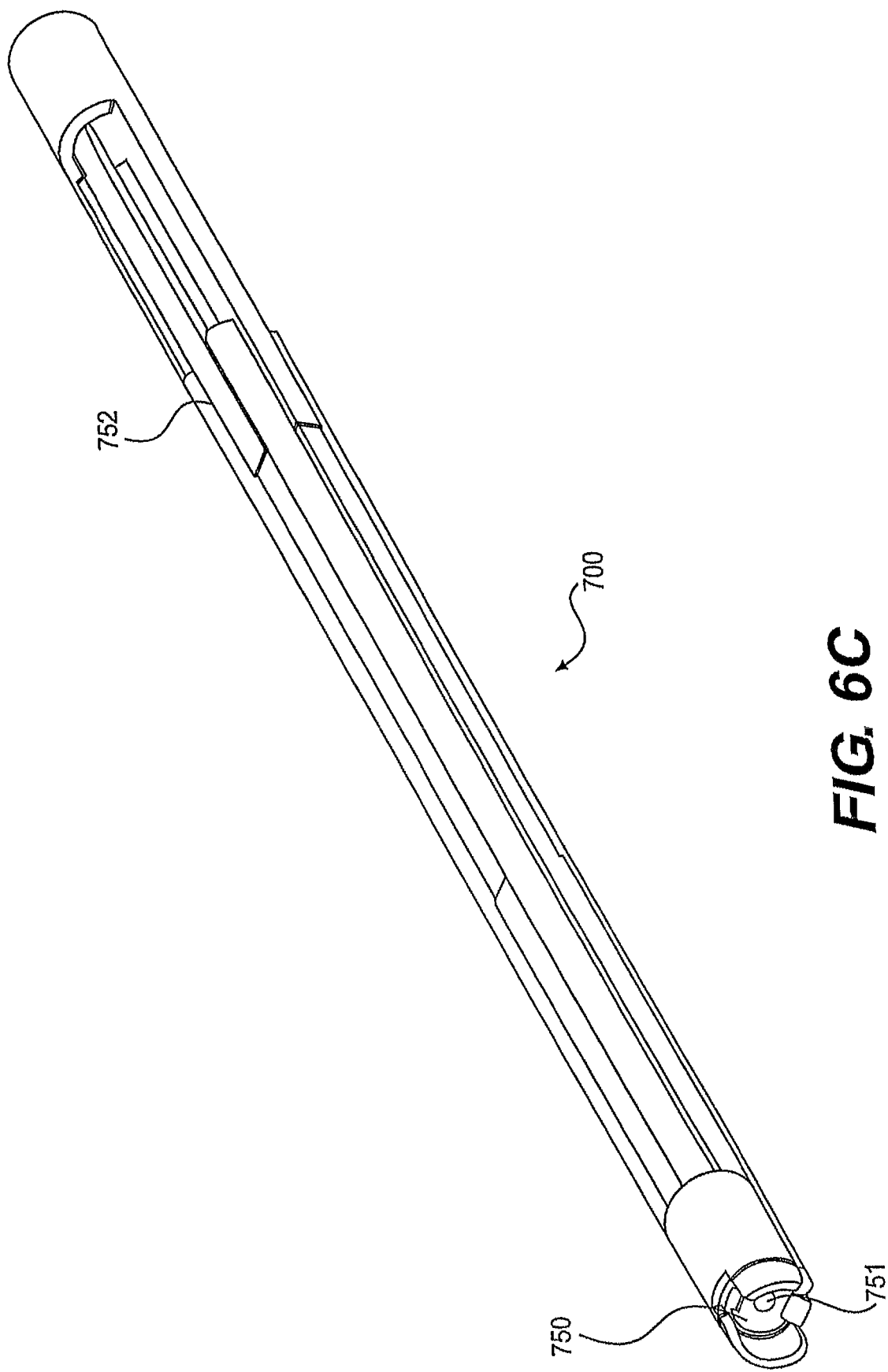
Figure 6D:
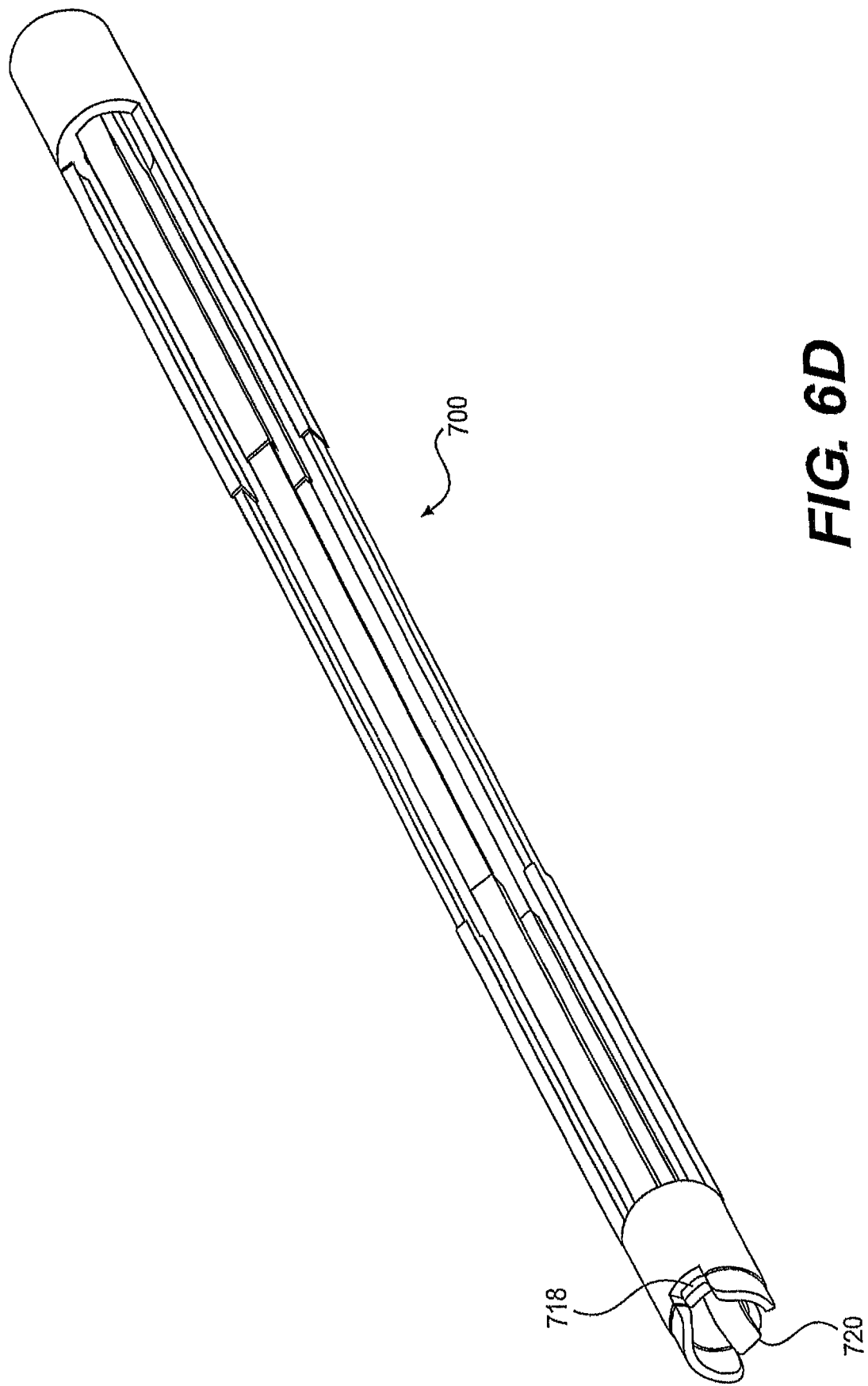

With reference now to FIG. 6C, assembly of electrode tube 702 within electrode 704 may be facilitated via a coaxial inner support 750. Support 750 may be formed from any suitable material. In one example, support 750 may be formed from a material stiff enough to lend structural rigidity as described herein. Further, support 750 may define a plurality of grooves 752 for receiving and retaining electrodes 706, 708, 722, 724 therein. Further, support 750 may define a longitudinal lumen 751 therethrough for receiving, e.g., a pull wire. Support 750 may provide structural rigidity to the entire assembly 700 so that bends 718, 720 may be formed during assembly. Further, support 750 may be configured to maintain a spacing between electrode tube 702 and 704 during assembly. This spacing may allow for routing and assembly of the aforementioned thermocouple wires and optional shrink tube covering for strain relief purposes.

Figure 7:
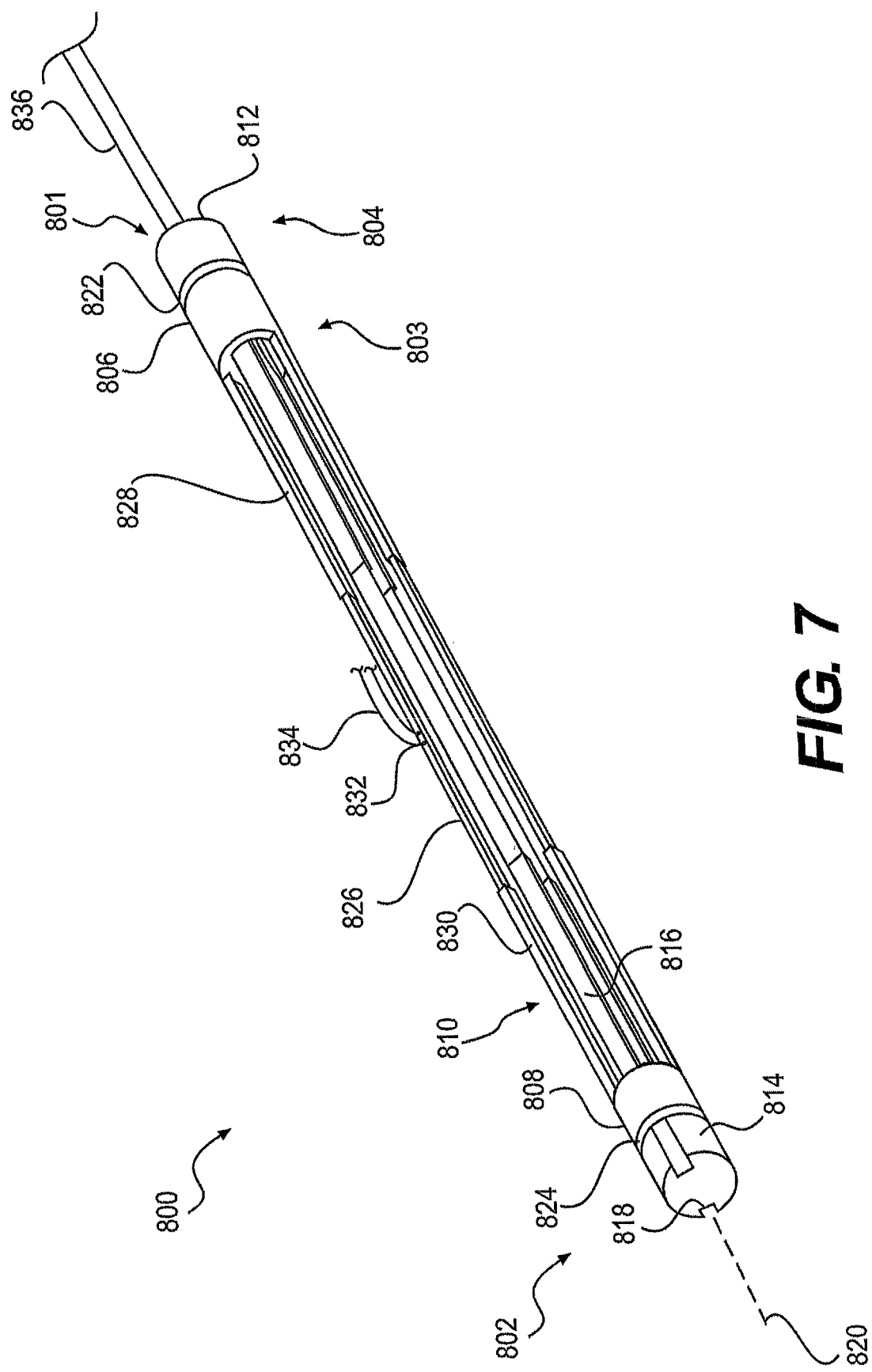
FIG. 7 is a perspective view of an energy delivery array in a collapsed configuration, according to another example of the present disclosure.

An energy delivery array 800 is shown in FIG. 7 in a collapsed configuration. Energy delivery array 800 may extend distally from one or more elongate members such as, e.g., sheaths, catheters, bronchoscopes, endoscopes, or the like. Energy delivery array 800 may extend from a proximal end 801 toward a distal end 802, and may include a first polar assembly 803 and a second polar assembly 804. Thus, in at least some examples, energy delivery array 800 may be configured to deliver bipolar energy (e.g., bipolar RF energy) from one polar assembly to another polar assembly that are insulated from one another. In one example, RF energy may be transferred from second polar assembly 804 through tissues of the body (e.g., tissues of the lung) to first polar assembly 803. However, it is also contemplated that RF energy may be transferred from first polar assembly 803 through tissues of the body to second polar assembly 804.

First polar assembly 803 may include a proximal end piece 806 and a distal end piece 808. Proximal and distal end pieces 806 and 808 may be formed of any suitable electrically conductive material, such as, e.g., metals or alloys including one or more of copper, steel, platinum, plastic materials with a conductive metal insert or coating, or the like. End pieces 806 and 808 may be formed from substantially the same materials, or from different materials, if desired. End pieces 806 and/or 808 may be substantially elongate, hollow cylindrical members, or may be formed in another suitable configuration. Proximal end piece 806 may be coupled to distal end piece 808 by one or more energy transfer elements 810. In the example shown in FIG. 7, two energy transfer elements 810 are shown coupling proximal end piece 806 to distal end piece 808, although other suitable configurations, e.g., one, three, or more energy transfer elements 810 also may be utilized.

Energy transfer elements 810 may be coupled to proximal and distal end pieces 806 and 808 by any suitable mechanism including, but not limited to, welding, soldering, machining, adhesives, crimping, laser attachment, or the like. Energy transfer elements 810 may be coupled to any suitable surface of proximal and distal end pieces 806 and 808 such as, e.g., a longitudinal end surface, an inner radial surface, an outer radial surface, or any other suitable surface. Energy transfer elements 810 may be radially spaced from one another relative to a longitudinal axis 820 of energy delivery array 800. Energy transfer elements 810 may be formed from any suitable material, such as those used to form proximal and distal end pieces 806 and 808. In some examples, energy transfer elements also may be formed of a shape memory metal or alloy, such as, e.g., nitinol.

Second polar assembly 804 may include a proximal end piece 812 and a distal end piece 814. Proximal and distal end pieces 812 and 814 may be formed of substantially similar materials as proximal and distal end pieces 806 and 808 of first polar assembly 803, or from different materials, if desired. End pieces 812 and/or 814 may be substantially elongate, hollow cylindrical members, or may be formed in another suitable configuration. Proximal end piece 812 may be coupled to distal end piece 814 by one or more energy transfer elements 816. In the example shown in FIG. 7, two energy transfer elements 816 are shown coupling proximal end piece 812 to distal end piece 814, although other suitable configurations, e.g., one, three, or more energy transfer elements 816 also may be utilized. Proximal end piece 812 of second polar assembly 804 may be disposed proximally of proximal end piece 806 of first polar assembly 803. Distal end piece 814 of second polar assembly 804 may be disposed distally of distal end piece 808 of first polar assembly 803. Thus, end pieces 806 and 808 of first polar assembly 803 may be disposed between (along longitudinal axis 820) end pieces 812 and 814 of second polar assembly 804.

Energy transfer elements 816 may be radially spaced from one another relative to longitudinal axis 820 of energy delivery array 800, and may be substantially similar to energy transfer elements 810 of first polar assembly 803, or may include a different configuration, if desired. Further, energy transfer elements 816 may be coupled to proximal and distal end pieces 812 and 814 in a substantially similar manner as energy transfer elements are coupled to proximal and distal end pieces 806 and 808 in first polar assembly 803.

In one example, however, energy transfer elements 816 may be received by recesses 818 formed in an outer radial surface of distal end piece 814. Similar to energy transfer elements 816, recesses 818 may be radially spaced from one another about longitudinal axis 820. In some examples, it is contemplated that proximal end piece 806, distal end piece 808, and proximal end piece 812 may alternatively or additionally include recesses formed in their respective outer radial surfaces for receiving an end of a given energy transfer element 810 or 816.

Energy transfer elements 810 may alternate with energy transfer elements 816 radially about longitudinal axis 820. Further, in some examples, energy transfer elements 810 may be disposed about a first circumference of energy delivery array 800, while energy transfer elements 816 may be disposed about a second circumference of energy delivery array 800. In one example, the first circumference may be spaced further from a central longitudinal axis (e.g., longitudinal axis 820) or radial center of electrode delivery array 800 than the second circumference. Thus, energy transfer elements 810 may be disposed further from a central longitudinal axis or radial center of energy delivery array 800 than energy transfer elements 816. However, it is contemplated that in some alternative examples, that energy transfer elements 816 may be disposed further from a central longitudinal axis (e.g., longitudinal axis 820) or radial center of energy delivery array 800 than energy transfer elements 810.

Each of energy transfer elements 810 and 816 may include an exposed active region 826 that is configured to deliver RF energy to body tissues. Active region 826 may be defined proximally and distally along energy transfer elements 810 and 816 by a proximal insulated region 828 and a distal insulated region 830. Along proximal insulated region 828 and distal insulated region 830, energy transfer elements 810 and 816 may be unable to deliver energy to bodily tissues. Proximal and distal insulated regions 828 and 830 may be formed from any suitable material, such as, e.g., a heat shrink sleeve, a dielectric polymeric coating, or other suitable material which may function as an insulator. Proximal and distal insulated regions may be coupled to energy transfer elements 810 and 816 by any suitable mechanism, such as, e.g., heat shrinking or the like.

The one or more active regions 826 of energy transfer elements 810 and/or 816 may include one or more temperature sensing elements 832. In one example, each active region 826 may include two temperature sensing elements 832 (e.g., thermocouples or the like), and each temperature sensing element 832 may include a lead 834 that is coupled to a controller and/or power source (not shown) of energy delivery array 800. Leads 834 may be routed proximally through proximal insulated regions 828, or in any other suitable configuration.

An activation element 836 may extend from proximal end 801 toward distal end 802 of energy delivery array 800. Activation element 836 may be substantially similar to activation element 104 described with reference to FIG. 5, and may be coupled to any suitable actuator. Activation element 836 may include expansion supporters (not shown) that are substantially similar to expansion supporters 106, 107 to maintain spacing between energy transfer elements 810 and 816. Activation element 836 may be coupled to distal end piece 814 in any suitable manner to facilitate movement of energy delivery array 800 between the collapsed configuration shown in FIG. 7 to a radially expanded configuration (not shown, but substantially similar to the expanded configuration of electrode cage 102 shown in FIG. 5). In some examples, activation element 836 may be pulled proximally, thereby moving distal end pieces 814 and 808 proximally to cause buckling and outward radial expansion of each of energy transfer elements 810 and 816. Thus, the longitudinal movement of activation element 836 may cause the radial expansion and contraction of energy delivery array 800.

Energy delivery array 800 may be configured to operate in a bipolar configuration, although other suitable configurations are also contemplated. First and second polar assemblies 803 and 804 may be insulated from one another by insulation elements 822 and 824. Insulation element 822 may be disposed between proximal end piece 806 of first polar assembly 803 and proximal end piece 812 of second polar assembly 804. Insulation element 824 may be disposed between distal end piece 808 of first polar assembly 803 and distal end piece 814 of second polar assembly 804. In some examples, insulation elements 822 and 824 may be generally disk shaped with a central aperture (e.g., insulating elements 822 and 824 may be insulating washers) although other suitable insulating configurations are also contemplated.

In some examples, activation element 836 may be configured to deliver energy from a controller and/or power source to distal end piece 814 and energy transfer elements 816 of second polar assembly 804. It is further contemplated that other activation elements (not shown) may also deliver energy to first polar assembly 802. In some examples, first polar assembly 803 and second polar assembly 804 may be separate poles of an RF circuit each with a different polarity supplied by the power source. In some examples, the polarities of the poles may oscillate at high frequency. As second polar assembly 804 may be insulated from first polar assembly 803, when energy delivery array is disposed within bodily lumens and tissues, RF energy may flow from second polar assembly 804, through bodily tissues, to proximal end piece 806, distal end piece 808, and energy transfer elements 816 of first polar assembly 803, heating the bodily tissues surrounding energy delivery array 800. Alternatively, energy may flow from first polar assembly 803, through bodily tissues, to second polar assembly 804.

Figure 8:
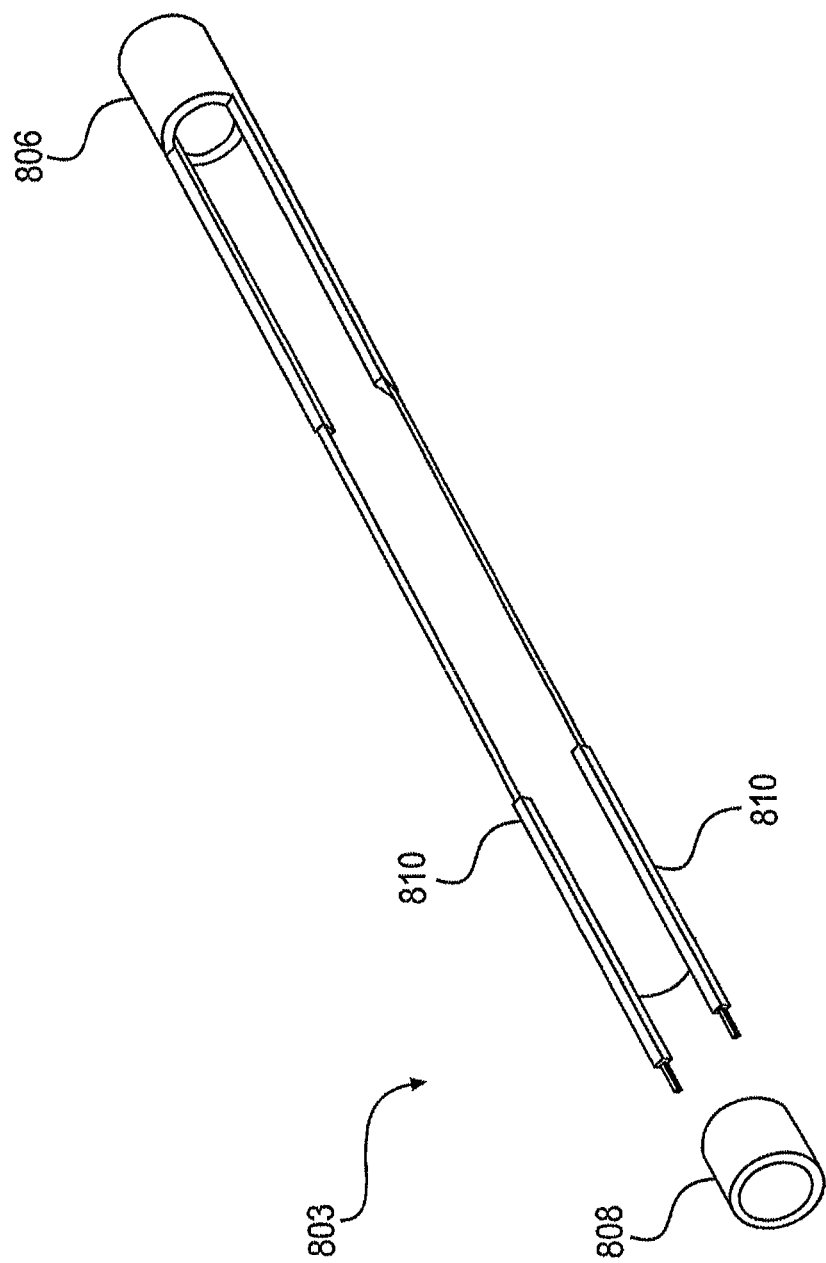
FIGS. 8-11 illustrate partially assembled views of an energy delivery array, such as the energy delivery array of FIG. 7.
Figure 9:
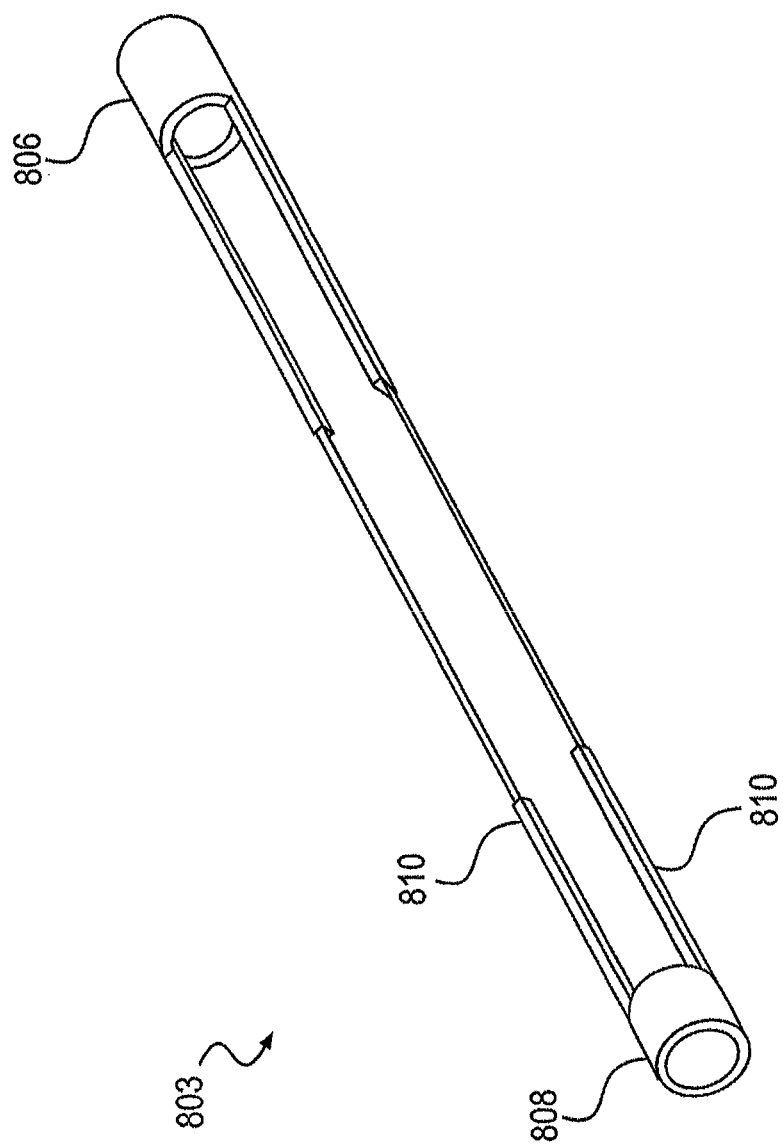
Figure 10:
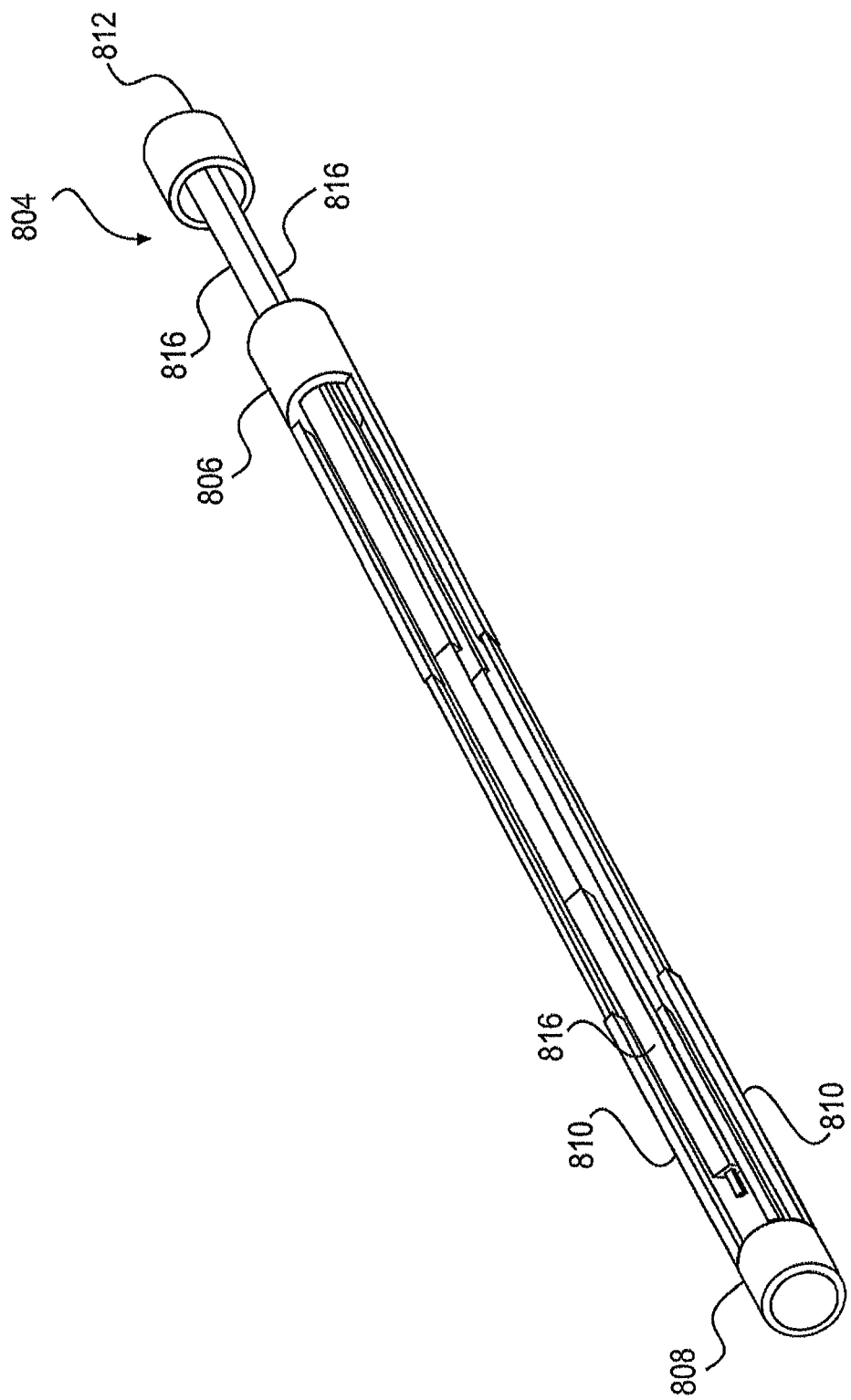
Figure 11:
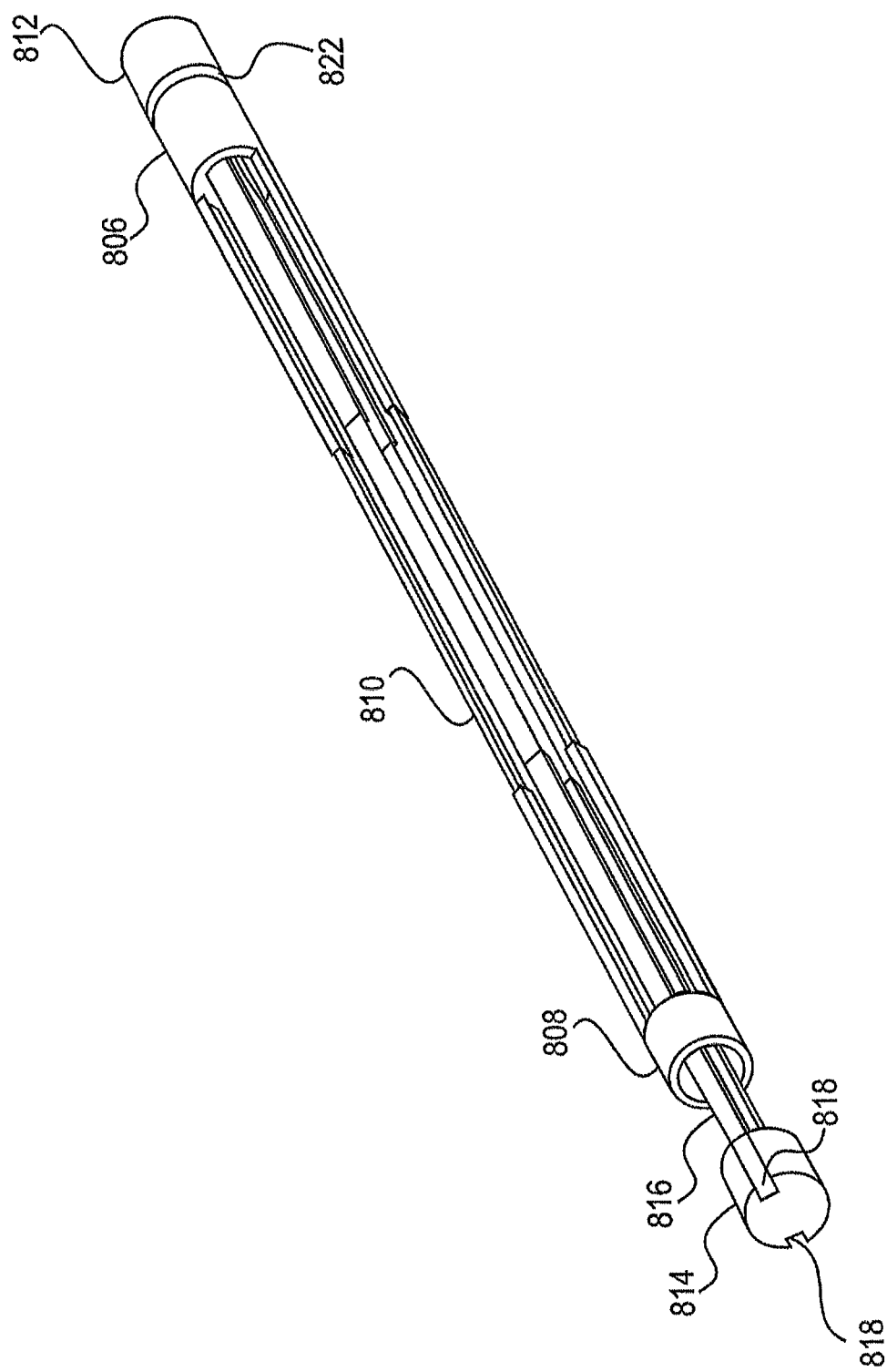

FIGS. 8-11 depict an exemplary assembly sequence of energy delivery array 800. FIG. 8 depicts a partially-assembled first polar assembly 803. As shown in FIG. 8, two energy transfer elements 810 may be coupled to proximal end piece 806. Distal end piece 808, which is shown unattached to energy transfer elements 810 in FIG. 8, may be attached to energy transfer elements 810 by any suitable mechanism described above to form first polar assembly 803 as shown in FIG. 9. Energy transfer elements 816 (shown already coupled to proximal end piece 812 in FIG. 10) may be inserted through a lumen defined by proximal end piece 806 toward distal end piece 808 of first polar assembly 803. As shown in FIG. 11, energy transfer elements 816 may be extended distally through a lumen of distal end piece 808 to distal end piece 814 of second polar assembly 804. Thus, in some examples, energy transfer elements 816 may be longer than energy transfer elements 810 to accommodate the assembly process described herein.

The various catheters, electrode arrays, energy delivery arrays, and other devices disclosed in the specification may be coupled to one or more shafts and/or sheaths having a length in a range from about 0.5 feet to about 8.0 feet, or another suitable length. In some examples, the energy delivery arrays and/or baskets may have an expanded basket diameter in a range from about 1 mm to about 25 mm, or in another suitable range. In some examples, the exposed portions of an electrode leg, e.g., active regions 826, may be about 5 mm in length. In other examples, active regions 826 may be in the range from about 1 mm to 50 mm in length, or may have another suitable length.

In various examples of the present disclosure, RF energy may be applied to tissues defining a body lumen (e.g., a lung airway) for a length of time in the range of about 0.1 seconds to about 600 seconds. In one example, a power source may be capable of delivering about 1 to 100 watts of RF energy, and may possess continuous flow capability. The tissues defining a lung airway may be maintained at a temperature that is lesser than, equal to, or greater than ambient body temperature. In one example, the tissues may be maintained at at least about 60° C., between 70° C. to 95° C., and/or between 70° C. to 85° C. The RF power-level may generally range from about 0-30 W, or another suitable range. In some examples, the power source may operate at up to a 75° C. setting. In some examples, RF energy may be delivered in discrete activations of, e.g., 5 to 10 seconds per activation. The frequency of the RF energy may be from 300 to 1750 kHz. It should be noted that, in at least some examples, other suitable values for energy delivery times, wattage, airway temperature, RF electrode temperature, and RF frequency are also contemplated.

Moreover, while specific examples may have been illustrated and described collectively herein, it should be appreciated that any subsequent arrangement designed to achieve the same or similar purpose may be substituted for the specific examples described and shown herein. This disclosure is intended to cover any and all subsequent adaptations or variations of the various examples. For example, it is contemplated that the above-described exemplary method steps can occur consecutively, simultaneously, or in various order with each other and with other steps that could be included. Combinations of the above examples, and other examples not specifically described herein, will be apparent to those of ordinary skill in the art upon reviewing the present disclosure.

Other examples of the present disclosure will be apparent to those skilled in the art from consideration of the specification and practice of the examples disclosed herein. It is intended that the specification and examples be considered as exemplary only, and departure in form and detail may be made without departing from the scope and spirit of the present disclosure as defined by the following claims.

What is claimed is:

1. A medical device, comprising:
an expandable electrode assembly reciprocally movable between a first configuration and a second configuration, the expandable electrode assembly including:

a first plurality of longitudinally extending legs formed in a first partially tubular member;
a second plurality of longitudinally extending legs formed in a second partially tubular member;
a first endpiece formed by first ends of the first and second partially tubular members; and
a second endpiece formed by second ends of the first and second partially tubular members, wherein a distal portion of the second partially tubular member overlaps an outer circumferential surface of a distal portion of the first partially tubular member.

2. The medical device of claim 1, wherein legs of the first partially tubular member circumferentially alternate with legs of the second partially tubular member.

3. The medical device of claim 1, wherein:
the first ends of the first and second partially tubular members are substantially C-shaped,
and the first endpiece is formed by inserting the first end of the second partially tubular member into a volume partially defined by the first end of the first partially tubular member.

4. The medical device of claim 3, wherein the first and second plurality of longitudinally extending legs define an expandable basket.

5. The medical device of claim 3, wherein the second end of the second partially tubular member further includes an offset that extends longitudinally beyond the second end of the first partially tubular member.

6. The medical device of claim 1, further including an activation element disposed through the first and second endpieces, the activation element configured to move the expandable electrode assembly radially outward from the first configuration to the second configuration, and reciprocally back to the first configuration.

7. The medical device of claim 6, wherein the activation element is electrically conductive and configured to deliver electrical energy to at least one of the first or second plurality of longitudinally extending legs.

8. The medical device of claim 1, wherein each leg of the first and second plurality of longitudinally extending legs includes:
a first insulated section;
a second insulated section; and
an exposed electrically conductive section between the first and second insulated sections.

9. The medical device of claim 8, wherein the first and second endpieces are insulated.

10. The medical device of claim 1, wherein:
the second end of the second partially tubular member includes a circumferentially extending gap between first and second C-shaped portions;
at least one of the second plurality of longitudinally extending legs extends from the first C-shaped portion; and
at least one of the second plurality of longitudinally extending legs extends from the second C-shaped portion.

11. The medical device of claim 10, wherein:
the first end of the first partially tubular member includes a circumferentially extending gap between first and second C-shaped portions;
at least one of the first plurality of longitudinally extending legs extends from the first C-shaped portion of the first partially tubular member; and
at least one of the first plurality of longitudinally extending legs extends from the second C-shaped portion of the first partially tubular member.

12. The medical device of claim 1, wherein:
the first endpiece further includes a first longitudinally extending gap disposed between circumferential ends of the first endpiece; and
the second endpiece further includes a second longitudinally extending gap disposed between circumferential ends of the second endpiece,
wherein a proximal portion of the second partially tubular member overlaps an outer circumferential surface of a proximal portion of the first partially tubular member.

13. The medical device of claim 12, further including a tube disposed around at least one leg of the first or second plurality of legs.

14. The medical device of claim 13, further including a third longitudinally extending gap disposed in either the first end or the second end of the first partially tubular member, the tube extending through the third longitudinally extending gap when the expandable electrode assembly is in the second configuration, wherein the second configuration is an expanded configuration.

15. The medical device of claim 14, further including an endcap disposed through the first or second longitudinally extending gap, the endcap configured to prevent rotation of the first partially tubular member relative to the second partially tubular member.

16. A medical device, comprising:
a first partially tubular member including:
a first end;
a second end; and
a first plurality of legs extending between the first and second ends of the first partially tubular member,
wherein each of the legs of the first plurality of legs is formed integrally with each other and each of the first end and the second end of the first partially tubular member; and
a second partially tubular member including:
a first end;
a second end; and
a second plurality of legs extending between the first and second ends of the second partially tubular member,
wherein each of the legs of second plurality of legs is formed integrally with each other and each of the first end and the second end of the second partially tubular member,
wherein the first ends of the first and second partially tubular members are coupled together, wherein the first end of the second partially tubular member overlaps an outer circumferential surface of the first end of the first partially tubular member,
wherein the second ends of the first and second partially tubular members are coupled together, wherein the second end of the second partially tubular member overlaps an outer circumferential surface of the second end of the first partially tubular member, and
wherein the first and second plurality of legs are disposed about a longitudinal axis of the medical device,
wherein the first partially tubular member and the second partially tubular member are rotatable relative to one another to control a spacing between the first plurality of legs and the second plurality of legs.

17. The medical device of claim 16, wherein legs of the first partially tubular member circumferentially alternate with legs of the second partially tubular member.

18. The medical device of claim 16, wherein the first and second ends of the first and second partially tubular members are C-shaped.

19. A medical device, comprising:
an expandable electrode assembly reciprocally movable between a first configuration and a second configuration, the expandable electrode assembly including:
a first end part extending only partially around a circumference of the medical device;
a second end part extending only partially around the circumference of the medical device, wherein a portion of the second end part overlaps a portion of the first end part;
a first plurality of longitudinally extending legs coupled to the first end part; and
a second plurality of longitudinally extending legs coupled to the second end part,
wherein the first end part radially surrounds the second end part, and wherein the first end part and the second end part are rotatable relative to one another to control a spacing between the first plurality of longitudinally extending legs and the second plurality of longitudinally extending legs.

20. The medical device of claim 19, wherein legs of the first plurality of longitudinally extending legs circumferentially alternate with legs of the second plurality of longitudinally extending legs.

\* \* \* \* \*